US006527769B2

(12) United States Patent
Langberg et al.

(10) Patent No.: US 6,527,769 B2
(45) Date of Patent: Mar. 4, 2003

(54) TISSUE ABLATION SYSTEM AND METHOD FOR FORMING LONG LINEAR LESION

(75) Inventors: Jonathan J. Langberg, Atlanta, GA (US); James C. Peacock, III, San Carlos, CA (US); Michael D. Lesh, Mill Valley, CA (US)

(73) Assignee: Atrionix, Inc., Palo Alto, CA (US)

( * ) Notice: Subject to any disclaimer, the term of this patent is extended or adjusted under 35 U.S.C. 154(b) by 0 days.

(21) Appl. No.: 10/083,317

(22) Filed: Feb. 25, 2002

(65) Prior Publication Data

US 2002/0082595 A1 Jun. 27, 2002

Related U.S. Application Data

(62) Division of application No. 09/260,316, filed on Mar. 1, 1999, now abandoned.
(60) Provisional application No. 60/076,562, filed on Mar. 2, 1998.

(51) Int. Cl.[7] ................................................ A61B 18/18
(52) U.S. Cl. ......................... 606/41; 606/47; 607/101; 607/122
(58) Field of Search ............................ 604/528; 606/41, 606/42, 45–50; 600/374, 585; 607/100–102, 122

(56) References Cited

U.S. PATENT DOCUMENTS

| 5,431,649 A | 7/1995 | Mulier et al. |
| 5,593,405 A | 1/1997 | Osypka |
| 5,607,462 A | 3/1997 | Imran |
| 5,687,723 A | 11/1997 | Avitall |
| 5,702,438 A | 12/1997 | Avitall |
| 5,741,249 A | 4/1998 | Moss et al. |
| 5,797,842 A | 8/1998 | Pumares et al. |
| 5,971,983 A | 10/1999 | Lesh |
| 6,012,457 A | 1/2000 | Lesh |
| 6,024,740 A | 2/2000 | Lesh et al. |
| 6,071,274 A * | 6/2000 | Thompson et al. ......... 607/122 |
| 6,071,279 A | 6/2000 | Whayne et al. |
| 6,161,543 A | 12/2000 | Cox et al. |
| 6,214,002 B1 | 4/2001 | Fleischman et al. |
| 6,237,605 B1 | 5/2001 | Vaska et al. |

FOREIGN PATENT DOCUMENTS

| EP | 0 727 184 A1 | 8/1996 |
| WO | WO 95/15115 | 8/1995 |

* cited by examiner

*Primary Examiner*—Linda C. M. Dvorak
*Assistant Examiner*—David M. Ruddy
(74) *Attorney, Agent, or Firm*—Knobbe, Martens, Olson & Bear, LLP

(57) ABSTRACT

The present invention relates to a tissue ablation device assembly which is adapted to form a conduction block along a length of tissue between two predetermined locations along the left atrial wall. The assembly comprises an ablation element on an elongated ablation member that is coupled to each of two delivery members, wherein the delivery members are adapted to controllably position and secure the ablation element along the length of tissue between the predetermined locations. A linear lesion in the tissue between the predetermined locations is then formed by actuation of the ablation element. The invention further provides that the ablation member may slideably engage one or two delivery members such that an adjustable length of the ablation element along the ablation member may be extended externally from the engaged delivery member and along a length of tissue.

16 Claims, 15 Drawing Sheets

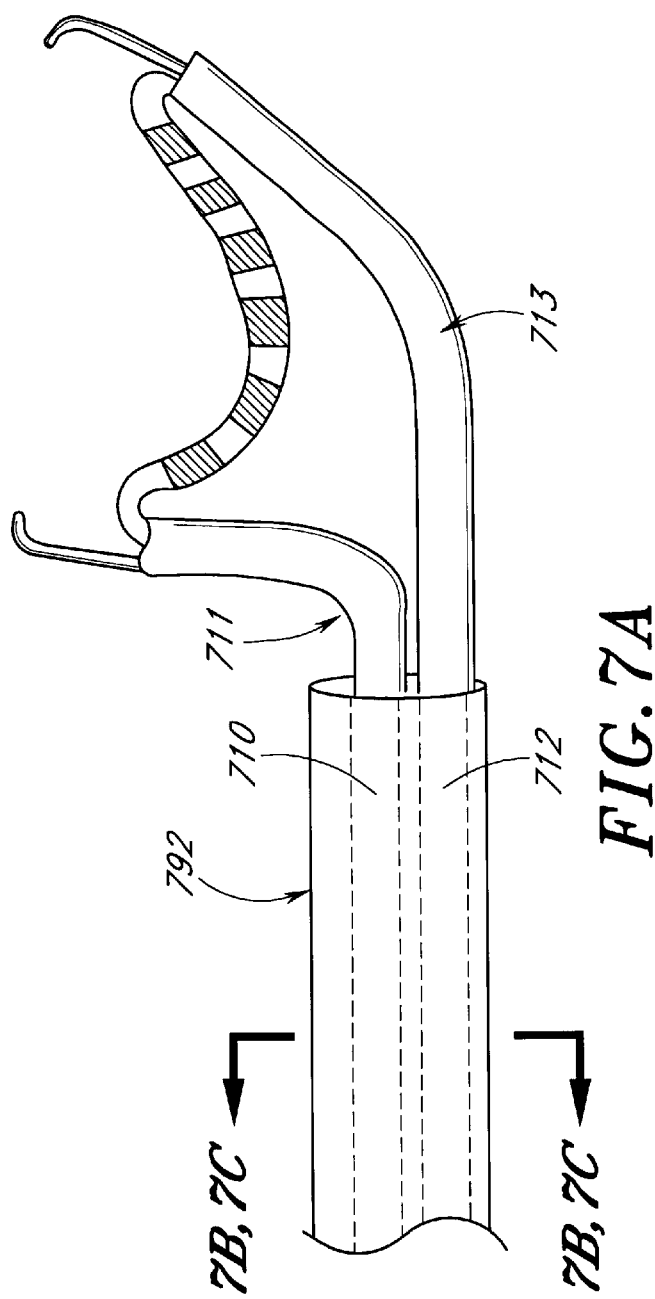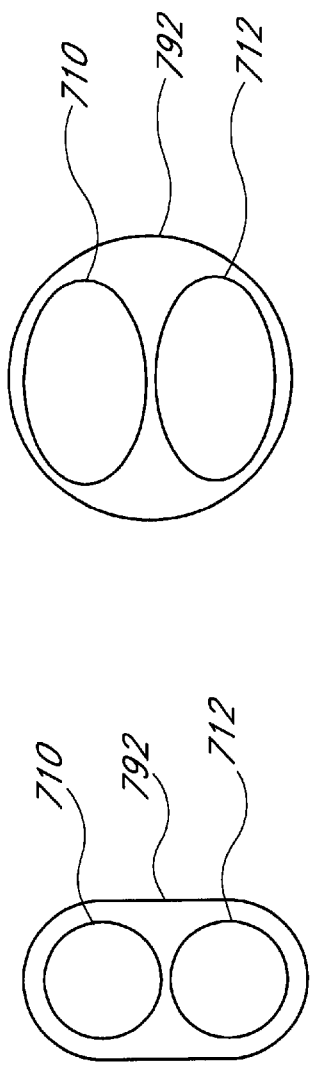
FIG. 7A
FIG. 7B
FIG. 7C

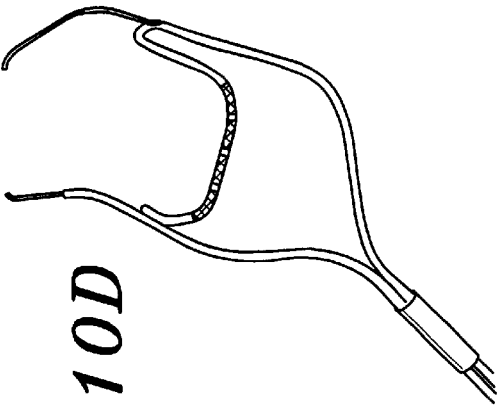
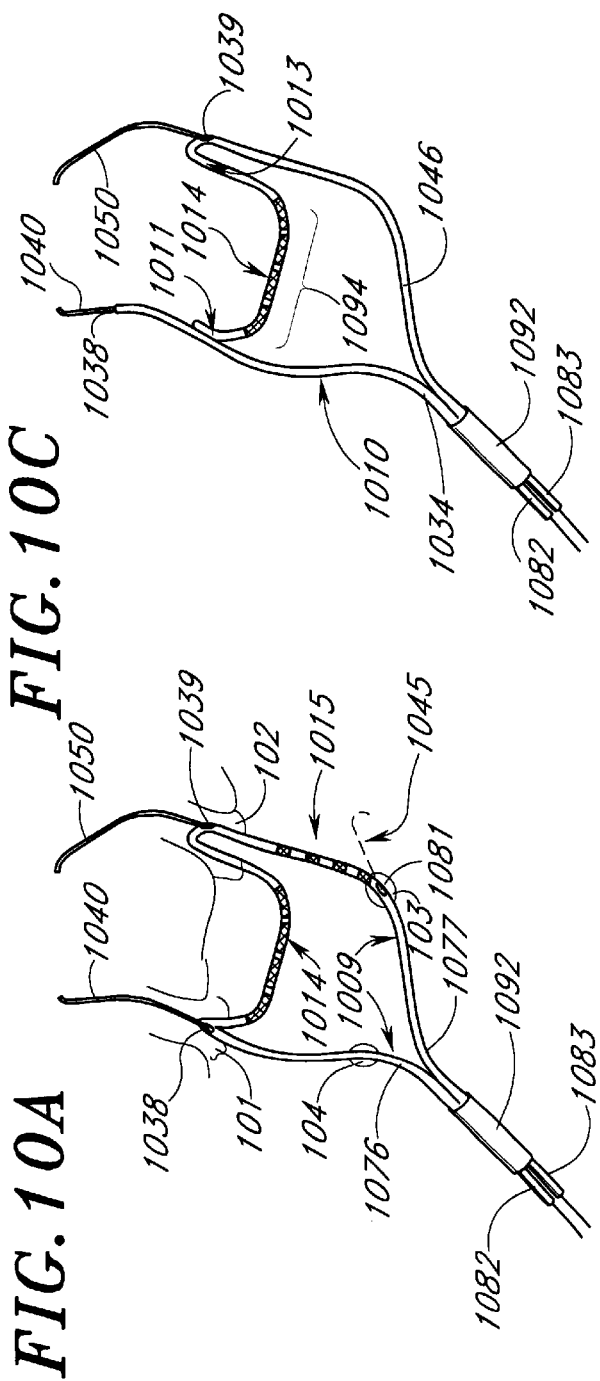
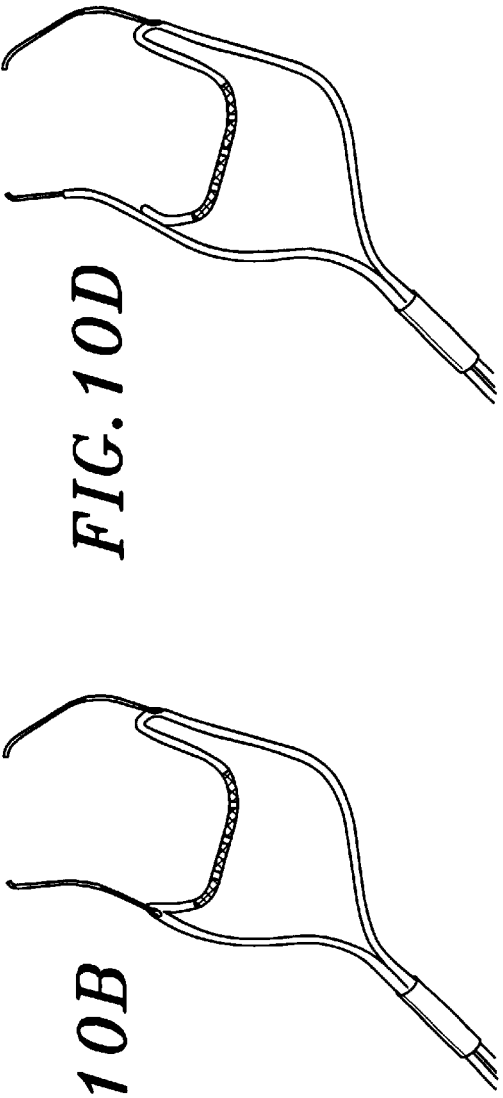

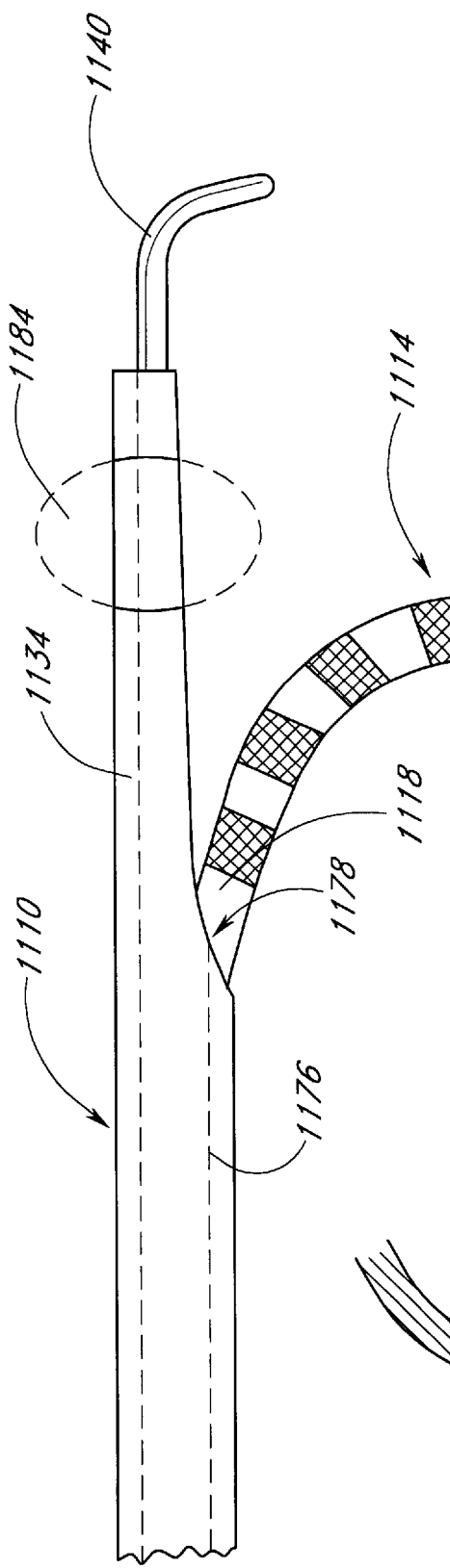

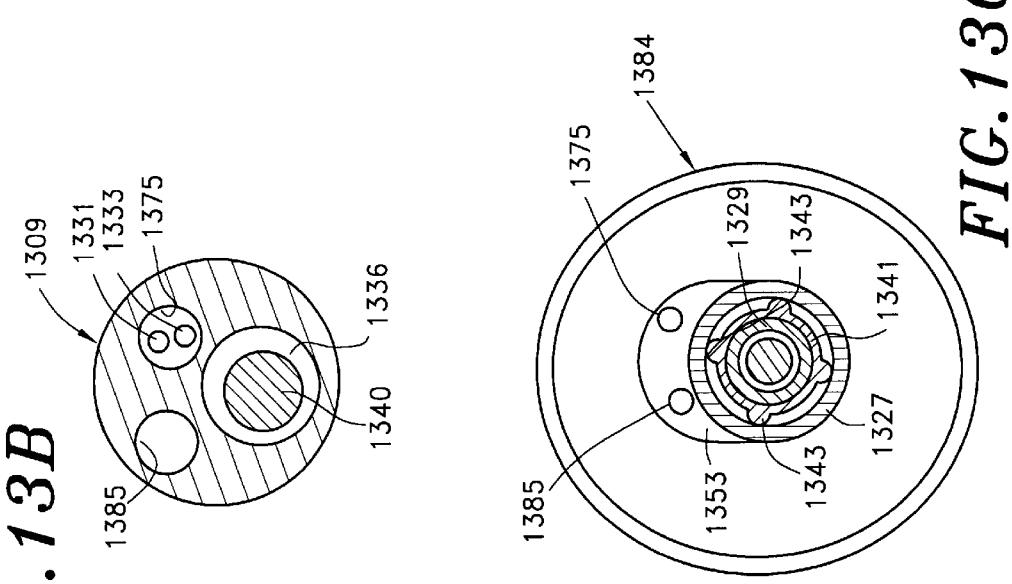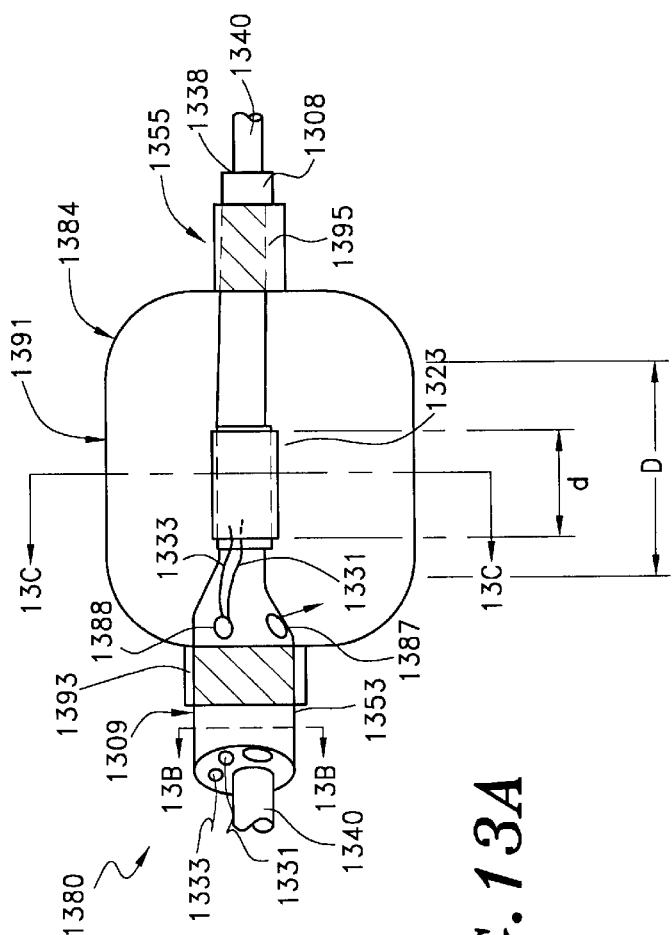

TISSUE ABLATION SYSTEM AND METHOD FOR FORMING LONG LINEAR LESION

RELATED APPLICATIONS

This application is a division of application Ser. No. 09/260,316, filed on Mar. 1, 1999, now abandoned which claims priority under §119(e) to provisional application No. 60/076,562, filed on Mar. 2, 1998.

BACKGROUND OF THE INVENTION

The present invention relates to a surgical device and more specifically, to a tissue ablation assembly that is adapted to form a conduction block along a length of tissue between two predetermined locations along a left atrial wall.

Cardiac arrhythmia's, particularly atrial fibrillation, are a pervasive problem in modern society. Although many individuals lead relatively normal lives despite persistent atrial fibrillation, the condition is associated with an increased risk of myocardial ischemia, especially during strenuous activity. Furthermore, persistent atrial fibrillation has been linked to congestive heart failure, stroke, and other thromboembolic events. Thus, atrial fibrillation is a major public health problem.

Normal cardiac rhythm is maintained by a cluster of pacemaker cells, known as the sinoatrial ("SA") node, located within the wall of the right atrium. The SA node undergoes repetitive cycles of membrane depolarization and repolarization, thereby generating a continuous stream of electrical impulses, called "action potentials." These action potentials orchestrate the regular contraction and relaxation of the cardiac muscle cells throughout the heart. Action potentials spread rapidly from cell to cell through both the right and left atria via gap junctions between the cardiac muscle cells. Atrial arrhythmia's result when electrical impulses originating from sites other than the SA node are conducted through the atrial cardiac tissue.

In most cases, atrial fibrillation results from perpetually wandering reentrant wavelets, which exhibit no consistent localized region(s) of aberrant conduction. Alternatively, atrial fibrillation may be focal in nature, resulting from rapid and repetitive changes in membrane potential originating from isolated centers, or foci, within the atrial cardiac muscle tissue. These foci exhibit centrifugal patterns of electrical activation, and may act as either a trigger of paroxysmal atrial fibrillation or may even sustain the fibrillation. Recent studies have suggested that focal arrhythmia's often originate from a tissue region along the pulmonary veins of the left atrium, and even more particularly in the superior pulmonary veins.

Several surgical approaches have been developed for the treatment of atrial fibrillation. One particular example, known as the "maze" procedure, is disclosed by Cox, JL et al. "The surgical treatment of atrial fibrillation. I. Summary", *Thoracic and Cardiovascular Surgery* 101(3):402–405 (1991) and also by Cox, J L "The surgical treatment of atrial fibrillation. IV. Surgical Technique", *Thoracic and Cardiovascular Surgery* 101(4):584–592 (1991). In general, the maze procedure is designed to relieve atrial arrhythmia by restoring effective SA node control through a prescribed pattern of incisions about the cardiac tissue wall. Although early clinical studies on the maze procedure included surgical incisions in both the right and left atrial chambers, more recent reports suggest that the maze procedure may be effective when performed only in the left atrium (see for example Sueda et al., "Simple Left Atrial Procedure for Chronic Atrial Fibrillation Associated With Mitral Valve Disease" (1996)).

The left atrial maze procedure involves forming vertical incisions from the two superior pulmonary veins and terminating in the region of the mitral valve annulus, traversing the inferior pulmonary veins en route. An additional horizontal incision connects the superior ends of the two vertical incisions. Thus, the atrial wall region bordered by the pulmonary vein ostia is isolated from the other atrial tissue. In this process, the mechanical sectioning of atrial tissue eliminates the atrial arrhythmia by blocking conduction of the aberrant action potentials.

The moderate success observed with the maze procedure and other surgical segmentation procedures have validated the principle that electrically isolating cardiac tissue may successfully prevent atrial arrhythmia's, particularly atrial fibrillation, resulting from either perpetually wandering reentrant wavelets or focal regions of aberrant conduction. Unfortunately, the highly invasive nature of such procedures may be prohibitive in many cases. Consequently, less invasive catheter-based approaches to treat atrial fibrillation through cardiac tissue ablation have been developed.

These less invasive catheter-based therapies generally involve introducing a catheter within a cardiac chamber, such as in a percutaneous translumenal procedure, wherein an energy sink on the catheter's distal end portion is positioned at or adjacent to the aberrant conductive tissue. Upon application of energy, the targeted tissue is ablated and rendered non-conductive.

The catheter-based methods can be subdivided into two related categories, based on the etiology of the atrial arrhythmia. First, focal arrhythmia's have proven amenable to localized ablation techniques, which target the foci of aberrant electrical activity. Accordingly, devices and techniques have been disclosed which use end-electrode catheter designs for ablating focal arrhythmia's centered in the pulmonary veins, using a point source of energy to ablate the locus of abnormal electrical activity. Such procedures typically employ incremental application of electrical energy to the tissue to form focal lesions. The second category of catheter-based ablation methods are designed for treatment of the more common forms of atrial fibrillation, resulting from perpetually wandering reentrant wavelets. Such arrhythmia's are generally not amenable to localized ablation techniques, because the excitation waves may circumnavigate a focal lesion. Thus, the second class of catheter-based approaches have generally attempted to mimic the earlier surgical segmentation techniques, such as the maze procedure, wherein continuous linear lesions are required to completely segment the atrial tissue so as to block conduction of the reentrant wave fronts.

An example of an ablation method targeting focal arrhythmia's originating from a pulmonary vein is disclosed by Haissaguerre et al. in "Right and Left Atrial Radiofrequency Catheter Therapy of Paroxysmal Atrial Fibrillation" in *Journal of Cardiovascular Electrophysiology* 7(12), pp. 1132–1144 (1996). Haissaguerre et al. describe radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and were ablated using a standard 4 mm tip single ablation electrode.

Another ablation method directed at paroxysmal arrhythmia's arising from a focal source is disclosed by Jais et al. "A focal source of atrial fibrillation treated by discrete radiofrequency ablation" *Circulation* 95:572–576 (1997). At the site of arrhythmogenic tissue, in both right and left atria, several pulses of a discrete source of radiofrequency energy were applied in order to eliminate the fibrillatory process.

Application of catheter-based ablation techniques for treatment of reentrant wavelet arrhythmia's demanded development of methods and devices for generating continuous linear lesions, like those employed in the maze procedure. Initially, conventional ablation tip electrodes were adapted for use in "drag burn" procedures to form linear lesions. During the "drag" procedure, as energy was being applied, the catheter tip was drawn across the tissue along a predetermined pathway within the heart. Alternatively, lines of ablation were also made by sequentially positioning the distal tip electrode, applying a pulse of energy, and then re-positioning the electrode along a predetermined linear pathway.

Subsequently, conventional catheters were modified to include multiple electrode arrangements. Such catheters typically contained a plurality of ring electrodes circling the catheter at various distances extending proximally from the distal tip of the catheter.

While feasible catheter designs existed for imparting linear ablation tracks, as a practical matter, most of these catheter assemblies have been difficult to position and maintain placement and contact pressure long enough and in a sufficiently precise manner in the beating heart to successfully form segmented linear lesions along a chamber wall. Indeed, many of the aforementioned methods have generally failed to produce closed transmural lesions, thus leaving the opportunity for the reentrant circuits to reappear in the gaps remaining between point or drag ablations. In addition, minimal means have been disclosed in these embodiments for steering the catheters to anatomic sites of interest such as the pulmonary veins. Subsequently, a number of solutions to the problems encountered with precise positioning, maintenance of contact pressure, and catheter steering have been described. These include primarily the use of (1) preshaped ablating configurations, (2) deflectable catheter assemblies, and (3) transcatheter ablation assemblies.

One approach to improved placement has been to use preshaped configurations which impart various predetermined lesion patterns, such as "hairpins" or "J-shapes". Typically, these configurations are situated at the distal end of various steering catheters. Such catheters generally include steering wires, extending from a steering mechanism at the proximal end of the catheter to an anchor point at the distal end of the catheter. By applying tension to the steering wires, the tip of the catheter can be directed in a desired direction. Furthermore, some catheters comprise a rotatable steering feature which allows the catheter as a whole to be rotated about its longitudinal axis, by manipulating the proximal end of the catheter. This exerts a torque which translates to a rotating motion at the distal end which allows a laterally deflected distal tip to be rotated. Once the catheter is steered and positioned to a desired site within an atrial chamber, ablating elements may be activated to form the lesion.

Some preshaped catheter assemblies employ a flexible outer sheath which is advanced over the distal end of the preshaped "guide" catheter. Movement of the guide catheter within the sheath modifies the predetermined curve of the distal end of the catheter. By inserting different shaped guide catheters through the outer sheath, different shapes for the distal end of the catheter are created. In one embodiment, the guide catheter position is visualized by X-ray fluoroscopy and progressively repositioned in real time by remote percutaneous manipulation along a preferred pathway in the moving wall of a beating atrium to form continuous lesions.

Deflectable catheter configurations adapted to form curvilinear lesions within an atrial chamber, include devices having a three dimensional basket structure that encloses an open interior at the distal end of the device. The deflectable basket elements may carry single or multiple electrodes. The baskets may be deployed from the catheter by removal of a sheath, done by manipulating the steering assembly located at the proximal end of the catheter. Such deflectable catheter assemblies may form elongated lesions, or simple or complex patterns of curvilinear lesions, depending on the pattern of ablating electrodes on the basket elements. Curvilinear elements may be deployed individually in succession to create the desired maze pattern. In further embodiments, curvilinear elements may include a family of flexible, elongated ablating elements which are controlled by a steering mechanism thereby permitting the physician to create flexes or curves in the ablating elements. Such curvilinear elements include a variety of ablating electrode configurations including linear ribbons and closely wound spirals. A further variation includes the use of gripping members which serve to fix the position of the ablation surface against the atrial wall. The gripping members may include teeth or pins to enhance the ablation of the cardiac tissue by maintaining a substantially constant pressure against the heart tissue to increase the uniformity of the ablation.

Transcatheter-based assemblies include systems for creating both linear lesions of variable length or complex lesion patterns. Such assemblies and methods involve catheter systems which can adapt to the tissue structures and maintain adequate contact and which are easily deployable and maneuverable. One example of a transcatheter-based assembly and method for creating complex lesion patterns includes the use of flexible electrode segments with an adjustable coil length which may form a convoluted lesion pattern of varying length. This device includes a composite structure which may be flexed along its length to form a variety of curvilinear shapes from a generally linear shape.

Other transcatheter ablation assemblies include the use of steerable vascular catheters which are expanded to conform to the surface of the cardiac chamber. One such expandable system comprises single or multiple proximally constrained diverging splines which expand upon emergence from the distal end of a catheter sheath, like the deflectable basket assembly described above. The splines are sufficiently rigid to maintain a predisposed shape but are adapted to be deflected by contact with the cardiac chamber wall. This expandable multi-electrode catheter is adapted to be positioned against the inner wall of a cardiac chamber to create linear continuous lesions.

Another example describes an expandable structure and method for ablating cardiac tissue, including a bendable probe which is deployed within the heart. The probe carries at least one elongated flexible ablation element, a movable spline leg and further including a bendable stylet in a single loop support structure. The assembly provides for tension to bend the stylet which then flexes the ablation element into a curvilinear shape or other readily controlled arcuate catheter shapes to allow a close degree of contact between the electrode elements and the target tissue for forming long, thin lesion patterns in cardiac tissue.

An additional example of a bendable transcatheter assembly comprises an outer delivery sheath and an elongated EP device slideably disposed within the inner lumen of the delivery sheath and secured at its distal end within the delivery sheath. The EP device has a plurality of electrodes on its distal portion. Proximal manipulation of the EP element causes the distal portion of the EP device to arch, or "bow" outwardly away from the distal section of the delivery sheath which engages the heart chamber, thereby forming a linear lesion in atrial wall.

None of the present catheter-based devices, however, include a tissue ablation assembly having two separate and independent delivery members with an elongated ablation member coupled therebetween. Nor does the prior art disclose an assembly where the ablation member is adapted to variably extend from a passageway through a distal port in one of the delivery members, thereby providing an ablation means having an adjustable length, extending between the first and second delivery members. Nor does the prior art disclose a method for securing the ablation member between a first and second anchor, thereby maintaining a desired linear position in contact with the atrial wall and facilitating the formation of a linear ablation track along the length of tissue between the anchors.

SUMMARY OF THE INVENTION

A tissue ablation device assembly is provided which is adapted to form a conduction block along a length of tissue between first and second predetermined locations along an atrial wall of an atrium in a patient.

According to one mode of the assembly, a first delivery member has a proximal end portion and a distal end portion with a first anchor, a second delivery member has a proximal end portion and a distal end portion with a second anchor, and an ablation member has first and second end portions and an ablation element between those end portions. The ablation member's end portions are engaged to the distal end portions of the first and second delivery members, respectively. In addition, the first and second anchors are adapted to secure the ablation element to the first and second predetermined locations in order to secure the ablation element along the length of tissue.

According to another mode of the assembly, first and second delivery members each have proximal and distal end portions, and an ablation member has first and second end portions with an ablation element between those end portions. The proximal end portions of the first and second delivery members are adapted to slideably engage a delivery sheath in a side-by-side arrangement. By manipulating the proximal end portion of the first delivery member externally of the body, the distal end portion of the first delivery member is adapted to controllably position the first end portion of the ablation member within the atrium and to secure the ablation element to the first predetermined location. Similarly, by manipulating the proximal end portion of the second delivery member externally of the body, the distal end portion of the second delivery member is adapted to controllably position the second end portion of the ablation member within the atrium and to secure the ablation element to the second predetermined location.

According to another mode of the assembly, a first delivery member has proximal and distal end portions and a passageway that extends between a distal port located along the distal end portion and a proximal port located proximally of the distal port. A second delivery member is also provided having proximal and distal end portions. An ablation member has a first end portion that is slideably engaged with an adjustable position within the passageway in the first delivery member, a second end portion that is engaged to the distal end portion of the second delivery member, and an ablation element with an ablation length located between the first and second end portions. Further to this mode, at least a portion of the ablation member which includes the ablation element is adapted to extend distally from the passageway through the distal port with an adjustable length extending between the first and second delivery members.

According to a further mode of the assembly, a first delivery member has a proximal end portion, a distal end portion with a first anchor, and a passageway that extends between a distal port located along the distal end portion and a proximal port located proximally of the distal port. An ablation member has a first end portion that is slideably engaged within the passageway with an adjustable position, and also has a second end portion which includes the ablation element that is adapted to extend distally from the passageway through the distal port with an adjustable length. The adjustable length between the distal port in the first delivery member and the second end portion of the ablation member is achieved by slideably adjusting the position of the first end portion of the ablation member within the passageway. Further to this mode, a second anchor is also located along the second end portion of the ablation member. The first and second anchors of this assembly are adapted to secure the ablation element to the first and second predetermined locations, respectively, such that at least a portion of the ablation length is secured to and extends along the length of tissue.

In one further aspect of the modes just described, a tracking member for tracking over a guidewire or other guidemember is included with the first or second delivery member, or the first or second anchor. Alternatively, a guidewire tracking member may be provided for each of two of these assembly components, thereby adapting the assembly to track over two wires in order to string the ablation element between adjacent vessels respectively engaged by those wires. Further to this aspect, one or more guidewire tracking members has a passageway for tracking over a guidewire and which terminates in a distal port. Accordingly, the ablation member may be engaged to the guidewire tracking member either at or adjacent to the distal port or proximally thereof.

In another aspect of the modes just described, first and second actuating members are positioned within the first and second delivery members. Each actuating member terminates proximally at a proximal coupler along the proximal end portion of the respectively engaged delivery member, the proximal couplers being adapted to couple to an ablation actuator. In one variation of this aspect, the ablation element is an electrode element with one or more electrodes and each ablation actuating member is an electrical lead wire. In another variation, the ablation element includes an ultrasound transducer and each ablation actuating member is an electrical lead which is coupled to a different surface on that transducer.

BRIEF DESCRIPTION OF THE DRAWINGS

FIG. 7A is a perspective view of another tissue ablation assembly in accordance with the present invention, illustrating delivery through a transeptal sheath in a transeptal left atrial ablation procedure.

FIGS. 7B–C schematically show two alternative cross-sectional shapes for the delivery members of the tissue ablation assembly shown in FIG. 7A.

FIG. 10A is a perspective view of another tissue ablation assembly in accordance with the present invention, during delivery through a transeptal delivery sheath.

FIG. 10B is a perspective view illustrating a variation of the assembly shown in FIG. 10A.

FIG. 10C is a perspective view of another variation of the assembly shown in FIG. 10A.

FIG. 10D is a perspective view of another variation of the assembly shown in FIG. 10C.

FIG. 11A is a perspective view of another tissue ablation assembly of the invention.

FIG. 11B is another perspective view of the tissue ablation assembly shown in FOG. 11A, illustrating the assembly during use in forming a lesion from a lower pulmonary vein to a mitral valve annulus.

FIG. 13A shows a sectioned cross-sectional view of a circumferential ablation member on the distal end portion of the delivery member, adapted for use in accordance with the tissue ablation assembly shown in FIG. 12.

FIG. 13B shows a transverse cross-sectional view taken along line 13B—13B through the elongate body of the delivery member shown in FIG. 13A.

FIG. 13C shows a transverse cross-sectional view taken along line 13C—13C through the circumferential ablation element along the circumferential ablation member shown in FIG. 13A.

DETAILED DESCRIPTION OF THE PREFERRED EMBODIMENTS

Definitions

Figure 1A:
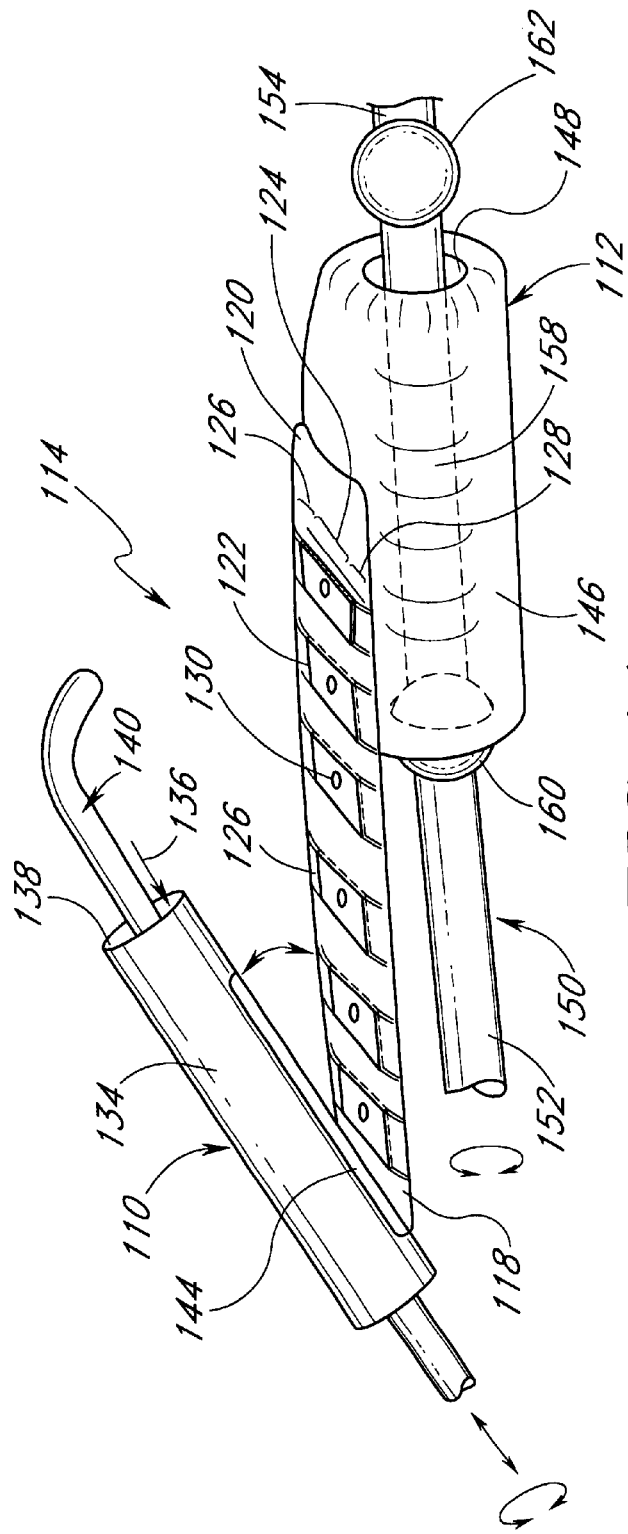
FIG. 1A shows an angular perspective view of a tissue ablation assembly comprising a ribbon shaped ablation member having a first end portion everted and secured to a first delivery member and a second end portion secured to a second delivery member.

The term "anchor" is herein intended to mean an element which is at least in part located in an anchoring region of the device and which is adapted to secure that region at a predetermined location along a body space wall. As such, "anchor" is intended to provide fixation as a securing means over and above a mere normal force against a single tissue surface which is created by confronting contact between the device and the tissue. Examples of suitable "anchors" within the intended meaning include (but are not limited to): an element that directly engages the tissue of the wall at the predetermined location such as by clamping, suctioning, or penetrating that tissue; and an element that is adapted to penetrate the plane of the body space wall, such as through an ostium of a vessel extending from the wall, for example, including a guidewire engaging or tracking member which provides a bore or lumen adapted to track a guidewire through an ostium of a lumen extending from the body space wall.

Furthermore, an expandable element, such as an expandable balloon or cage, is considered an anchor to the extent that it radially engages at least two opposite body space wall portions to secure the expandable element in place (such as opposite sides of a vessel). To the extent that the disclosure of the invention below is directed to any one particular anchoring element, it is contemplated that other variations and equivalents such as those described may also be used in addition or in the alternative to that particular element.

The term "guidewire" as used herein will be understood by those of skill in the art to cover any member which serves as a guide, including but not limited to a conventional guidewire, a catheter, a deflectable tip catheter, such as the type with distal end electrodes for mapping, as well as a hollow guide tube.

The term "ablation" or derivatives thereof is herein intended to mean the substantial altering of the mechanical, electrical, chemical, or other structural nature of the tissue. In the context of intracardiac ablation applications as shown and described with reference to the embodiments below, "ablation" is intended to mean sufficient altering of the tissue properties to substantially block conduction of electrical signals from or through the ablated cardiac tissue.

The term "element" within the context of "ablation element" is herein intended to mean a discrete element, such as an electrode, or a plurality of discrete elements, such as a plurality of spaced electrodes, which are positioned so as to collectively ablate an elongated region of tissue upon activation by an actuator.

Therefore, an "ablation element" within the intended meaning of the current invention may be adapted to ablate tissue in a variety of ways. For example, one suitable "ablation element" may be adapted to emit energy sufficient to ablate tissue when coupled to and energized by an energy source. Suitable examples of energy emitting "ablation elements" within this meaning include without limitation: an electrode element adapted to couple to a direct current (DC) or alternating current (AC) source, such as a radiofrequency (RF) current source; an antenna element which is energized by a microwave energy source; a heating element, such as a metallic element which is energized by heat such as by convection or current flow, or a fiber optic element which is heated by light; a light emitting element, such as a fiber optic element which transmits light sufficient to ablate tissue when coupled to a light source; or an ultrasonic element such as an ultrasound crystal element which is adapted to emit ultrasonic sound waves sufficient to ablate tissue when coupled to a suitable excitation source.

More detailed descriptions of radiofrequency (RF) ablation electrode designs which may be suitable in whole or in part as the ablating element according to the present invention are disclosed in U.S. Pat. No. 5,209,229 to Gillis; U.S. Pat. No. 5,487,385 to Avitall; and WO 96/10961 to Fleischman et al. More detailed descriptions of other energy emitting ablation elements which may be suitable according to the present invention are disclosed in U.S. Pat. No. 4,641,649 to Walinsky et al. (microwave ablation); and U.S. Pat. No. 5,156,157 to Valenta, Jr. et al. (laser ablation). The disclosures of these patents are herein incorporated in their entirety by reference thereto.

In addition, other elements for altering the nature of tissue may be suitable as "ablation elements" within the intended meaning of the current invention. For example, a cryoblation probe element adapted to sufficiently cool tissue to substantially alter the structure thereof may be suitable. Furthermore, a fluid delivery element, such as a discrete port or a plurality of ports which are fluidly coupled to a fluid delivery source, may be adapted to infuse an ablating fluid, such as a fluid containing alcohol, into the tissue adjacent to the port or ports to substantially alter the nature of that tissue. More detailed examples of cryoblation or fluid delivery elements such as those just described are disclosed in U.S. Pat. No. 5,147,355 to Friedman et al. and WO 95/19738 to Milder, respectively. The disclosures of these patents are incorporated in their entirety by reference thereto.

It is also to be further appreciated that the various embodiments shown and described in this disclosure collectively provide one beneficial mode of the invention, which mode is specifically adapted for use in the left atrium of a mammal. In this mode, the elongate ablation element is adapted to have its ends anchored in adjacent pulmonary vein ostia in the left atrium, with the elongate ablation element in substantial contact with the tissue that spans the length between those ostia. By subsequent ablation of the tissue between anchors in the adjacent ostia, a long linear lesion is created and provides a conduction block to electrical flow across the length of the lesion.

As will be appreciated from the more detailed disclosure of the embodiments below, a pattern of multiple long linear lesions between adjacent pulmonary vein ostia, and also including portions of the mitral valve annulus and septum, may be completed with the present invention. One pattern of such multiple ablation lesions can be considered a "box" of isolated conduction within the region of the pulmonary veins, and is believed to provide a less-invasive improvement and less traumatic alternative to the invasive "maze" surgical procedure previously described.

Tissue Ablation Assemblies

While a number of embodiments of the present invention are disclosed in detail, reference numerals are used consistently where possible. The first digit of each reference numeral refers to the embodiment of the assembly (e.g. (1) in FIG. 1 and (2) in FIG. 2), while the following digits refer to the specific component (e.g. 14 for the "ablation member"). Thus, for example, in the first embodiment of the tissue ablation assembly illustrated in FIG. 1A, the "ablation member" is labeled as 114, whereas a variation of the "ablation member" shown in FIG. 2A is referred to as 214.

Figures 2A, 2B:
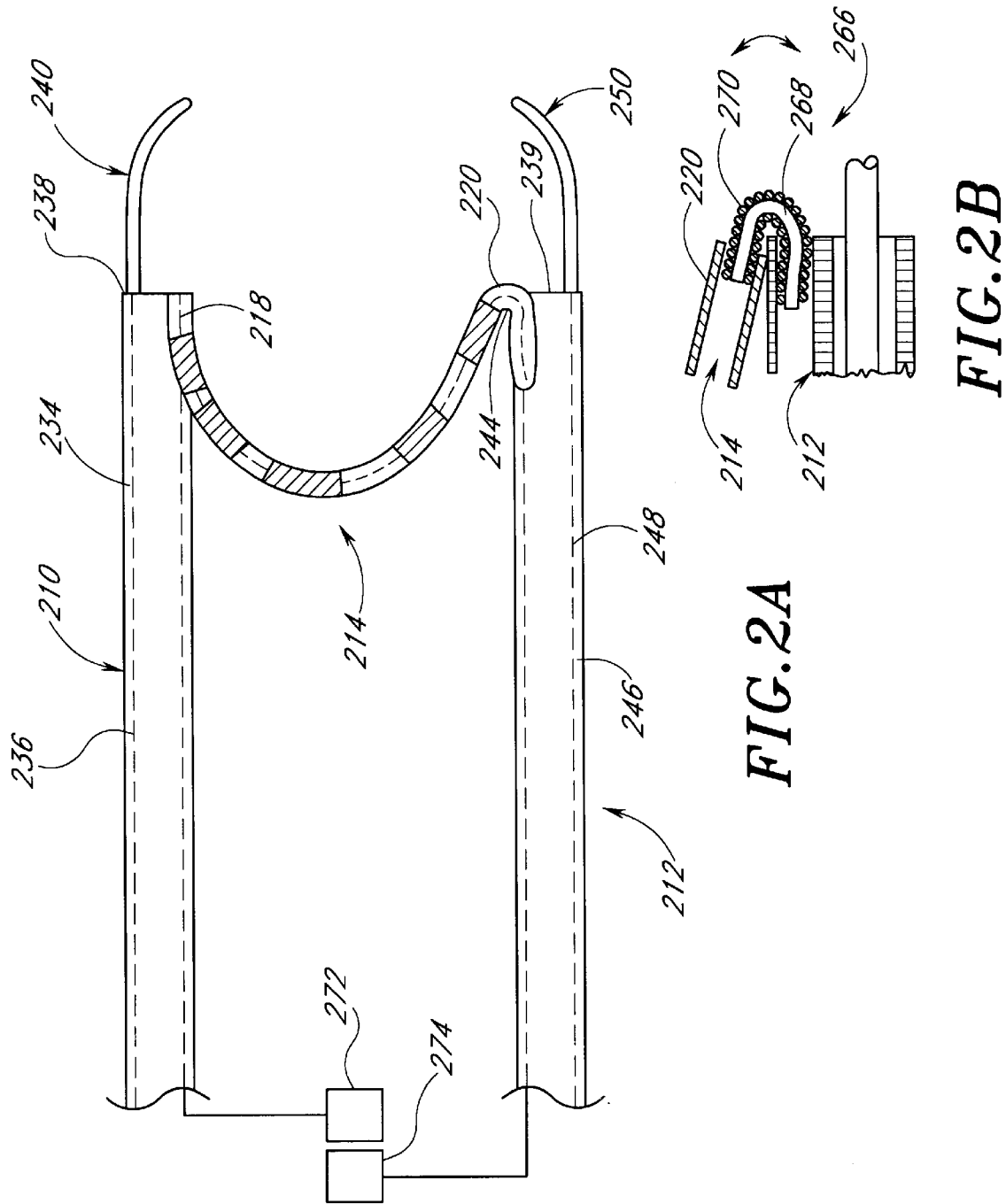
FIG. 2 shows a perspective view of another tissue ablation assembly of the present invention.

With reference to FIG. 1A, particular designs for first and second delivery members (110,112) and also for ablation member (114), are shown. A ribbon shaped member (116) has a first end portion (118) secured to a first delivery member (110) and a second end portion (120) secured to a second delivery member (112).

In a preferred aspect of the several embodiments herein described, the ablation member (114) is specifically provided as an electrode assembly with one or more electrodes (122) which traverses a length along the ablation member and which is adapted to engage the targeted length of tissue for ablation. The one or more electrodes are electrically coupled to at least one coupler along a proximal end portion of a delivery member via electrical lead wires extending along the delivery member. The proximal coupler is further adapted to couple to an ablation actuator, such as an RF current source.

The ablation actuator or actuators are engaged to the electrical coupler or couplers of the ablation device assembly and also to a ground patch (not shown). A circuit is thereby created which includes the ablation actuator, the electrode ablation element, the patient's body (not shown), and the ground patch which provides either earth ground or floating ground to the current source. In this circuit, an electrical current, such as an RF signal, may be sent through the patient between the electrode element and the ground patch, as would be apparent to one of ordinary skill.

In the specific embodiment shown in FIG. 1A, the ablation member (114) is shown to include a plurality of electrodes (122) in a spaced arrangement along the longitudinal axis of ablation member (114). A central region (124) is further bordered on either side by adjacent insulating regions (126,128). According to this design, the central region (124) is adapted to engage a length of tissue to be ablated while the adjacent insulating regions (126,128) engage adjacent lengths of tissue, thereby isolating the length of tissue from the blood pool during ablation. Electrodes (122) may also have an opposing surface (not shown) which is exposed in order to allow blood flow on a side opposite the active ablation surface to cool the electrode during ablation. Furthermore, electrode ports (130) are also shown in FIG. 1A on electrodes (122) and may provide a housing for sensing members (not shown), such as for example thermocouples or thermisters. In addition, or in the alternative, electrode ports (130) may also provide communication for fluid from an inner passageway to leak through the electrodes during ablation, such as for example to aid in cooling.

FIG. 1A further shows first and second delivery members (110,112) as having structurally different designs, although each design is adapted to engage the ablation element and to controllably position the ablation element by manipulating the proximal end portion of the respective delivery member.

In more detail to the design for first delivery member (110), as shown in FIG. 1A, a guidewire tracking member (134) is tubular and includes a guidewire lumen or passageway (136) between a distal guidewire port (138) and a proximal guidewire port (not shown) that is slideably engaged over a guidewire (140). The first end portion (118) of ablation member (114) is secured to the delivery member (110) at a location which is proximal to the distal guidewire port (138). The ablation member (114) also has a hinge point (144) which is either a preshaped hinge or is flexible to allow a certain degree of rotation and flexibility between the first delivery member (110) and the ablation member (114).

Figure 1B:
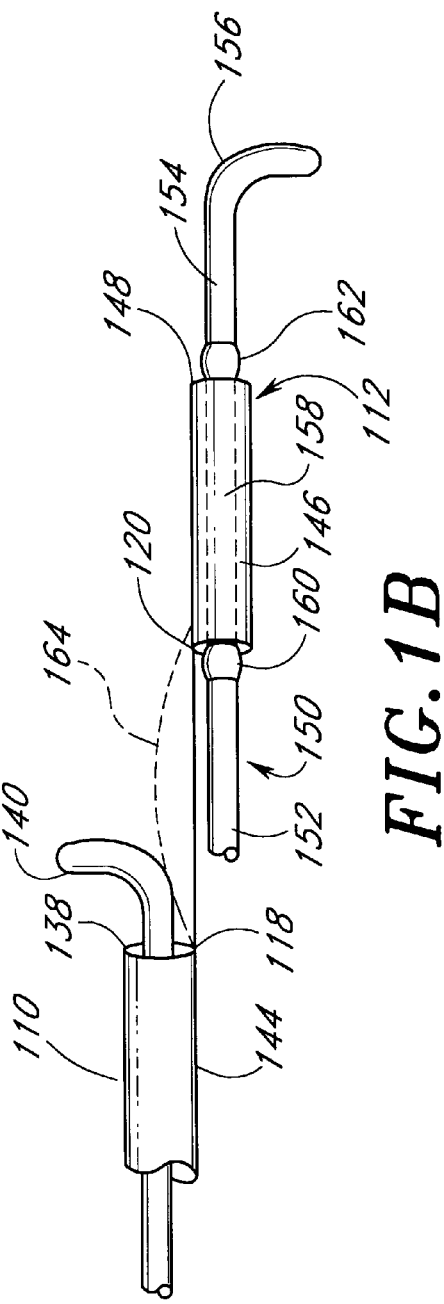
FIG. 1B shows a side perspective view of the tissue ablation assembly shown in FIG. 1A, except that the ablation member is shown extending between the first and second delivery members, in a direction parallel to the delivery members; an alternative bowed shape for the ablation member is shown in shadowed view, wherein the ablation member is adapted to flex.

In more detail to the design for a second delivery member (112), shown in FIG. 1A, a coupling or tracking member (146) is tubular and includes a lumen or passageway (148) that is slideably engaged over a guide member (150). The guide member includes a proximal guide portion (152) and a distal guide portion (154) which includes a shaped or shapeable tip (not show in FIG. 1A; 156 in FIG. 1B). The shapeable tip (156; FIG. 1B) is torsionally coupled to the proximal guide portion (152) such that the tip is steerable by torquing or rotating the guide member (150). In a preferred embodiment, the distal tip (156) of the guide member (150) is radiopaque under X-ray visualization, in order to facilitate its placement in a predetermined location. Also shown in shadow between proximal and distal guide portions is an intermediate coupling portion (158) which includes an extension of the guide member (150) and two spaced enlargements (160,162) over the guide member. The tubular coupling member (146) is also shown in FIG. 1A to coaxially house the guide member (150) between the two spaced enlargements (160,162). The guide member (150) is therefore rotatably engaged through the tubular coupling member (146), although with a limited range of motion relative to the tracking member's long axis due to the mechanical barriers at the enlargements (160,162). The ablation member (114) is secured to the tubular coupling member (146), with ablation member (114) extending from the engagement in a proximal orientation.

The various features of the FIG. 1A embodiment are believed to provide beneficial functionality in ablating a length of tissue between adjacent vessels, such as between pulmonary vein ostia in the left atrium.

In one example of the functional aspects of the design shown in FIG. 1A, both first and second delivery members (110,112) are adapted to controllably position the respectively engaged end portions of ablation member (114) within an atrium. More specifically, the first delivery member (110) is adapted to track over guidewire (140) in order to advance or withdraw from a pulmonary vein which is engaged by the guidewire. Consequently, the first delivery member is adapted to controllably place and remove the ablation element against a first point along the length of tissue to be ablated. The second delivery member (112) is also able to controllably place or remove the second end portion (120) of ablation member (114) within an adjacent pulmonary vein. However, in contrast to the "guide wire tracking" mechanism provided by the first delivery member (110), the second delivery member (112) utilizes a rotatable coupling design, whereby advancing and/or torquing the proximal guide portion (152) of guide member (150) allows one to maneuver the position of the shaped tip (156; FIG. 1B) into the vein. The limited range of longitudinal motion between the guide member (150) and the coupling member (146) permits the advancing or withdrawing of the proximal guide portion (152) to transmit these forces to the second end portion (120) of ablation member (114), thereby achieving controllable positioning of this member.

Another example of the functional aspects of the design shown in FIG. 1A is provided by the orientation of the ablation member (114) at each end where secured to the first and second delivery members (110,112). This relative orientation between component parts in the overall assembly allows the most distal portion of the delivery members to be seated deeply within a pulmonary vein while allowing each ablation member end to extend proximally out of the respective vein in order to traverse the adjoining region of atrial wall tissue. Moreover, the hinge point (144) for the ablation member on at least one of the delivery members also allows the assembly to "collapse" from a deployed position and to thereby allow the delivery members to fit in a "side-by-side" or relatively parallel arrangement within a delivery sheath during delivery into and out of the atrium. For the purpose of further illustrating this arrangement, FIG. 1A depicts the assembly in a configuration which is midway between a deployed configuration and a collapsed configuration for delivery, and further illustrates the motion of the hinge point (144) by way of an arrow adjacent thereto.

Notwithstanding the functional benefits just described for the specific embodiment shown in FIG. 1A, FIG. 1B shows another tissue ablation assembly with many similar components as those just described for FIG. 1A, although with slight modifications which are also believed to be beneficial in some applications.

In one aspect of the embodiment shown in FIG. 1B, the first end portion (118) of the ablation member (114) is shown secured to the first delivery member (110) with a distal orientation wherein the ablation member (114) extends distally from first delivery member (110). This distal orientation is believed to provide another beneficial design in order to accommodate the collapse of the assembly such that the delivery members (110,112) are in a side-by-side and relatively parallel relationship during delivery through a delivery sheath, as is further illustrated by the relatively collapsed configuration shown in FIG. 1B. Further to this orientation, a hinge point, such as shown at hinge point (144), may still provide a benefit at the engagement between ablation member (114) and first delivery member (110), although having a reverse role to the FIG. 1A embodiment, wherein the hinge point is relatively straight during delivery and is flexed and rotated during deployment of the assembly in the region of the pulmonary veins.

FIG. 1B also shows a shadowed view of an alternative shape (164) for ablation member (114) which is believed to provide a benefit in some applications. In particular, shape (164) is shown as a sweeping, curve or arc between the first and second end portions (118,120) of ablation member (114). By advancing guidewire tracking member (110) over guidewire (140) a first pulmonary vein leading from the atrium, and also advancing guide member (150) within a second adjacent pulmonary vein, the ablation member (114) is adapted to compress against the region of atrial wall tissue between the veins. It is believed that this compression may deflect the curved shape of ablation member (114) against a bias force along that curve and thereby provide a means for transmitting the force at the first and second end portions (118,120), due to forcing the respective delivery members distally, along the central regions of the ablation element to aid engagement to tissue along that region.

Further to the beneficial embodiments just shown and described by reference to FIGS. 1A–B, the specific arrangement of the overall assembly may be modified to form other beneficial devices which are further contemplated within the scope of the present invention. For example, the tissue ablation assembly shown in FIG. 2A, includes two delivery members which independently control the positioning of each of two ends of an ablation member (218,220), as was provided by the embodiment of FIGS. 1A–B. However, FIG. 2A shows first and second delivery members (210,212) to each include elongate bodies forming respective guidewire tracking members (234,246) with passageways (236,248; shown in shadow), respectively, extending between distal ports (238,239), also respectively, and proximal ports (not shown). First and second delivery members (210,212) are therefore adapted to slideably engage and track over guidewires (240,250), such as in order to position ablation member (214) along a length of tissue between pulmonary veins engaged by the guidewires. Moreover, it is believed that the inclusion of an elongate guidewire tracking member also provides a larger cross-sectioned member by which to push the respectively engaged end portion of the ablation member, thereby increasing the overall efficiency of contact along the ablation element length.

In addition, FIG. 2A shows first end portion (218) of ablation member (214) engaging first delivery member (210) with a proximal orientation and second end portion (220) engaging second delivery member (212) with a distal orientation, and is therefore adapted to adjust the configuration between a deployed position (as shown for example in FIG. 2A) and a delivery position in a similar manner as previously shown and described by reference to FIG. 1B. A hinge point (244) similar to hinge point (144) in FIG. 1A is also shown at the second end portion-second delivery member engagement, which hinge point is further shown in cross-sectional detail in one preferred embodiment in FIG. 2B which uses a coupling member (266).

Further to the coupling member (266), shown in FIG. 2B, a "U"-shaped core (268) with a coil (270) provided over its exterior surface engages second delivery member (212) and also engages end portion (220) of ablation member (214) such that ablation member (214) effectively extends with a proximal orientation away from the tip of delivery member. Further to this design, the core (268) may be a metallic core, such as for example a core made of an alloy of nickel and titanium, or of stainless steel, and the coil thereover may be of a variety of metals, such as stainless steel, platinum, or the like, whereas use of radiopaque coils such as platinum or tungsten may provide a visible marker at the location where the ablation member extends from the delivery member.

Coupling member may be adapted to the relative members by positioning the arms of the "U"-shaped member within seats provided by the other respectively coupled members, as is shown in FIG. 2B. In one method of making this transition, the wall forming the lumen is collapsed over the coupling member's arm, such as by heat shrinking the respective tubing over the coupling member's arm. Alternatively, an outer jacket (not shown) may be placed over the coupling member and also the respectively coupled other member and then heat shrunk to capture the engagement within that jacket. In addition, or in the alternative to both or either of these other methods, an adhesive may be used to pot the coupling member to the delivery and ablation members.

It is also to be further understood that other designs and materials may be used as a coupling member for the engagement between the ablation member and the delivery member. In one alternative, a pre-shaped member such as the previously described "U"-shaped core may be made of a heat-set polymer, such as a polyimide member formed into a bend shape. In another variation, a composite member may be used, such as for example a coil reinforced polymeric tubing, at the transition to form the hinge point (244). Moreover, notwithstanding the particular variations just described, other substitutes may also be suitable so long as a flexible hinge is established which allows seated engagement of the tip of the delivery member deep within a vessel such that the ablation member extends proximally therefrom so that it may engage the length of atrial wall tissue extending from the vein for ablation.

In one further beneficial aspect of the embodiment shown for delivery members (210,212) in FIG. 2B, an elongate body of the type shown for each delivery member may allow for additional passageways or lumens besides just the guidewire lumens, which additional passageways may further allow for additional components along the devices which may further facilitate the ablation process. For example, passageways (236,248) are shown in shadow along first and second delivery members (210,212), respectively, in FIG. 2A. In more detail to the variation shown in FIG. 2A, multiple ablation actuating members (not shown) may extend along these passageways which are adapted to couple to ablation element (214) and also to a proximal coupler (not shown) that is further adapted to couple to an ablation actuator, as is shown schematically at individual ablation actuators (272,274) coupled to each delivery member, although the various actuating members may also couple to a single common ablation actuator.

In addition, each of the guidewire tracking members (234,246) shown in FIG. 2A, and also shown previously (134) for the first delivery member in FIGS. 1A and B, is adapted to receive the respective guidewire through its lumen such that the guidewire extends externally of the catheter's elongate body on either side of the region of slideable engagement. This arrangement, however, is merely one example of a broader functional structure of the guidewire tracking variation illustrated by the anchors of FIG. 2A. Considering this variation more generally, bores are formed at each of the distal and intermediate regions of the elongate body. Each bore is adapted to track over a guidewire separately and independently of the other bore. Each bore generally has two open ends or ports, and the respectively. engaged guidewire extends through the bore and externally of the device from each bore end.

According to the general structure just described, the specific guidewire tracking member embodiments of FIG. 2A, and otherwise where appropriate to the embodiments, may be modified according to one of ordinary skill without departing from the scope of the invention. For example, a cuff or looped tether of material may be provided at the desired anchoring location along the elongate body and thereby form a bore that is adapted to circumferentially engage a guidewire according to the description above. More particularly, a metallic ring, or a polymeric ring such as polyimide, polyethylene, polyvinyl chloride, fluoroethylpolymer (FEP), or polytetrafluoroethylene (PTFE) may extend from the elongate body in a sufficient variation. Or, a suitable strand of material for forming a looped bore for guidewire engagement may also be constructed out of a filament fiber, such as a Kevlar or nylon filament fiber. One more specific example of such an alternative guidewire tracking member which may be suitable for use in the current invention, particularly as a distal guidewire tracking member, is disclosed in U.S. Pat. No. 5,505,702 to Arney; incorporated herein by reference.

Figure 3:
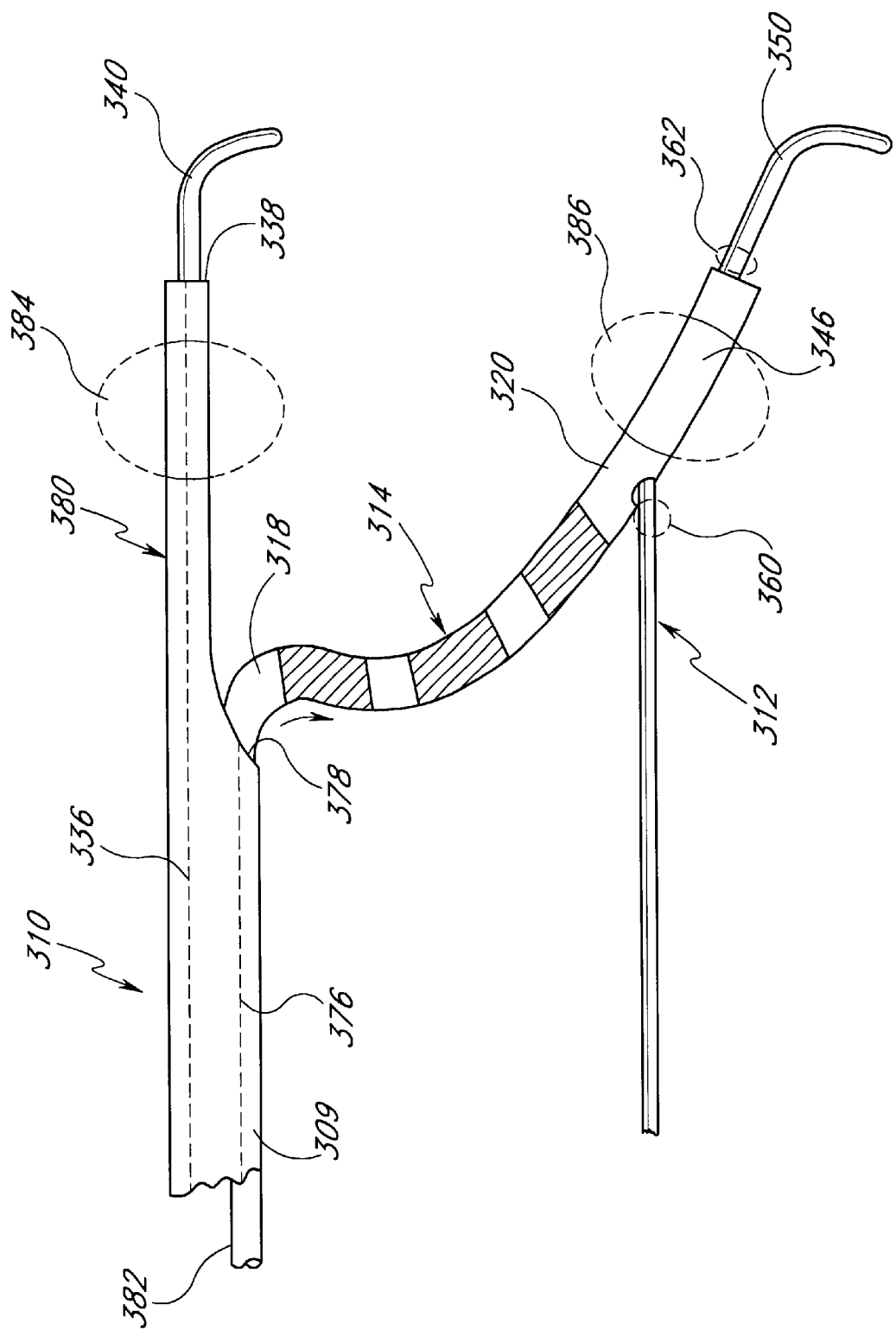
FIG. 3 shows a perspective view of another tissue ablation assembly in accordance with the present invention.

With reference to FIG. 3, an embodiment of another overall mode of a tissue ablation assembly is shown, wherein an ablation member (314) has its first end portion (318) coaxially and slideably engaged within a passageway (376) through a first delivery member (310).

In more detail to FIG. 3, first delivery member (310) has an elongate body (309) which forms a guidewire tracking member that includes a guidewire lumen or passageway (336) extending between a distal guidewire port (338) and a proximal port (not shown). A first guidewire (340) is slideably engaged within the guidewire passageway (336). A second passageway (376) also extends along the elongate body (309) between a distal port (378), which is located along distal end portion (380) proximally of distal guidewire port (338) and a proximal port (not shown) located proximally of the distal port. Central to this embodiment, an ablation member (314) is adapted to the first delivery member (310) such that its first end portion (318) is slideably engaged within a passageway (376). According to this relationship, the ablation member (314) has adjustable positioning within the passageway with remote manipulation of a region of the first end portion (382) which extends externally of the body by a user. As such, the second end portion (320) is adapted to extend an adjustable length externally of the passageway (376) from distal port (378) and between first delivery member (310) and second delivery member (312). Further to this adjustable positioning, it is further contemplated that the ablation element along the ablation member may also be adjusted to extend entirely out from the passageway, or only a portion may extend externally between the delivery members. It is believed that this arrangement beneficially allows for a variable distance between the anchors formed by guidewire tracking members. In addition, it has been observed that, by pulling on the first end portion of the ablation member once both anchors or guidewire tracking members are engaged within vessels, a "cinching" action may be achieved which tightens the ablation member and guidewire tracking anchors along the tissue between the anchors.

Also shown in the embodiment of FIG. 3 is a second guide tracking member (346) along the second end (320) of ablation member (314) which is slideably engaged over a second guidewire or guide member (350). Further to second guide tracking member (346), FIG. 3 also shows, in shadow, two enlargements (360,362) on guide member (350) which border either end of tracking member (346) to form a similar type of guide member-coupling member arrangement for a delivery member to that previously shown and described by reference to FIGS. 1A–B.

Moreover, either one of the enlargements (360,362) may also be provided at the exclusion of the other for the purpose of allowing a stop within a vessel against which the ablation member can abut when advanced, in the case of providing only enlargement (362), or for allowing a stop that can be used to engage and push ablation member (314) distally with the guide member, in the case of providing only enlargement (360). Further to the latter purpose, which holds true for the case of providing either both enlargements (360,362) or only enlargement (360), a further beneficial variation not shown provides a robust pushing member for the proximal guide member portion of the guide member (350). In one such variation not shown, a hypotube of metal such as stainless steel or nickel titanium alloy is provided proximally of enlargement (360), and may for example transition into a core wire in the distal regions, such as at a location proximally adjacent to enlargement (362). Such transition may be achieved for example by welding, soldering, adhering, or swaging or otherwise securing and affixing a core wire to and/or within the bore of a hypotube according to that variation. In another variation, the core wire may transition from a large diameter portion proximally of the enlargement (360), to a tapered transition into a smaller diameter portion such as at or distally of enlargement (362).

In addition, FIG. 3 shows in shadowed view that each of the first delivery member (310) and the guide tracking member (346) formed by the second end of ablation member (314) further include expandable members (384,386). Each of the expandable members is adapted to adjust from a radially collapsed condition during delivery into an atrium or vessel extending therefrom, and to a radially expanded condition which is adapted to circumferentially or otherwise radially engage a vessel wall to secure the respective anchor there. For further illustration, such expandable members may be inflatable balloons, or may be other suitable substitutes according to the anchoring purpose put forth, such as for example a mechanically expandable cage. Moreover, it is to be further understood by reference to the other embodiments, particularly where a distal end portion extends distally from a point of engagement with an ablation member, that such expandable members as just described by reference to FIG. 3 may be equally suited for use in combination with the specific components of those particular other assemblies and embodiments.

Figure 4:
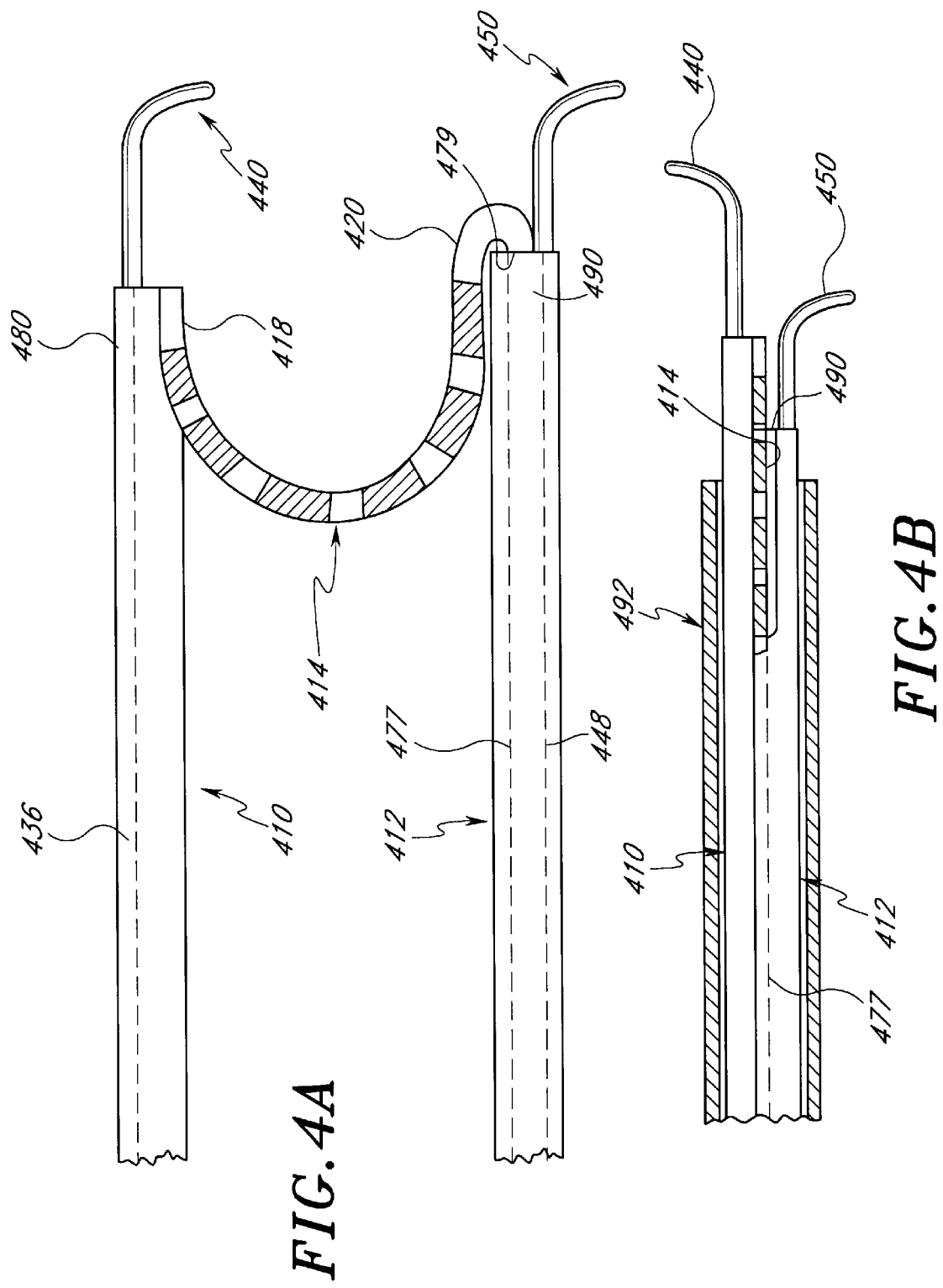
FIG. 4A shows a perspective view of another tissue ablation assembly of the present invention.
FIG. 4B is a perspective view of the same tissue ablation assembly shown in FIG. 4A, illustrating a delivery mode of the assembly.

A further tissue ablation assembly is shown in FIG. 4A and includes two elongate delivery members (410,412) with an ablation member (414) extending therebetween, and essentially combines the side-by-side elongate body dual delivery member design, as previously shown and described by reference to FIG. 2A, together with a coaxially housed, slideably engaged ablation member design of FIG. 3. Both first and second delivery members (410,412) have guidewire tracking passageways (436,448) for slideably engaging guidewires (440,450). However, in a further modification, a first end (418) of ablation member (414) is affixed to a distal portion (480) of the first delivery member (410), whereas the second end (420) of ablation member (414) extends from and is slideably engaged within passageway (477) in the second delivery member (412), via a distal port (479) located at the distal tip (490) of the second delivery member (412).

According to the particular arrangement of the assembly of FIG. 4A, the assembly is further shown in the partially segmented view in FIG. 4B in a collapsed condition during delivery within and through a delivery sheath (492). Further to this delivery mode of operation, ablation member (414) is adapted to be substantially housed within passageway (477) through distal port (479) by either advancing second delivery member (412) or withdrawing ablation member (414) until distal port (479) abuts against the engagement between first end portion (418) of ablation member and the distal end portion (480) of the first delivery member (410). The second end portion (420) of the ablation member (414) is withdrawn into the passageway (477) in the second delivery member (412).

Figure 5:
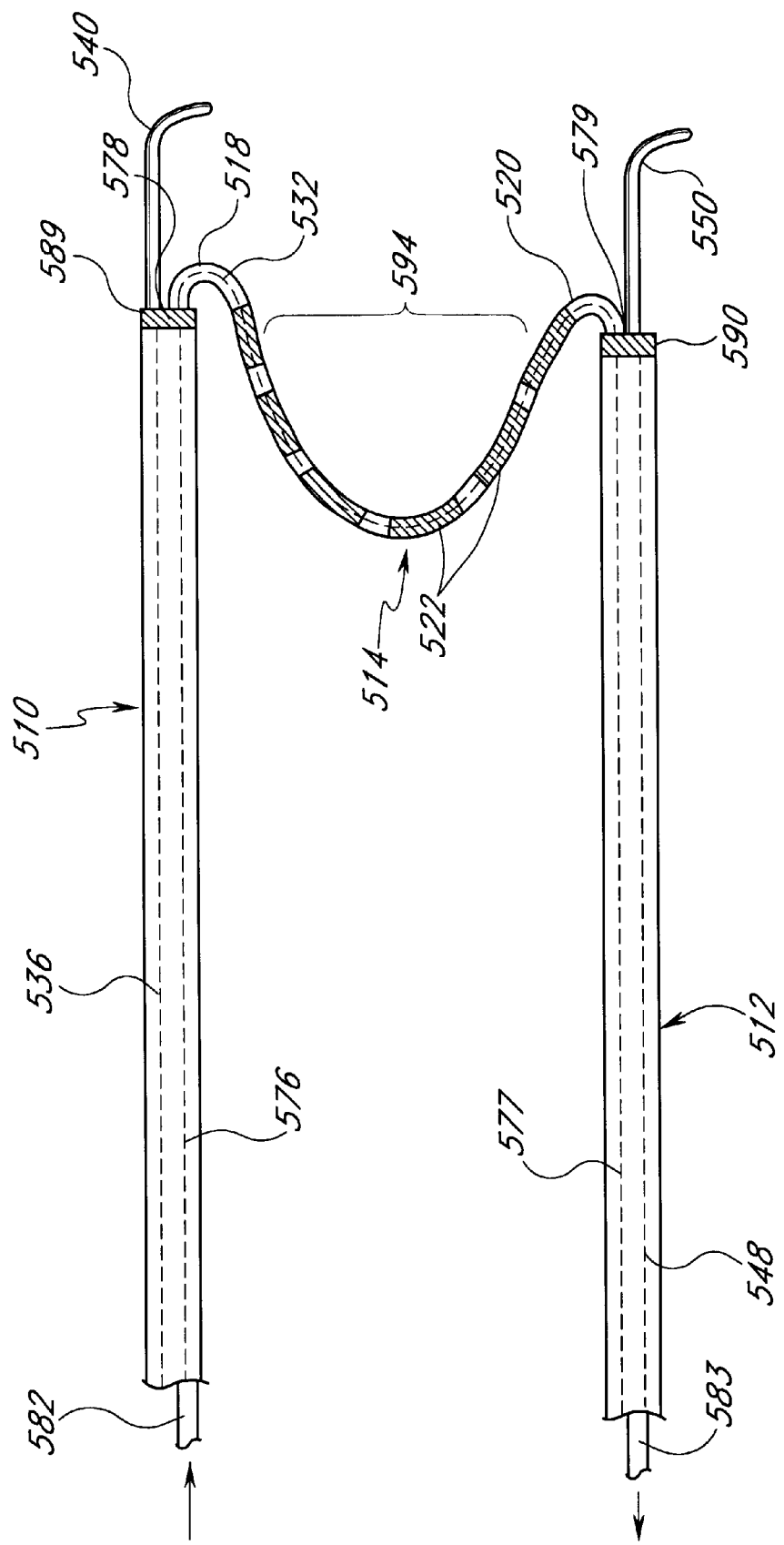
FIG. 5 shows a perspective view of another tissue ablation assembly in accordance with the present invention.

Still a further tissue ablation assembly is shown in FIG. 5 and further modifies the assembly shown in FIGS. 4A–B to include a coaxial engagement between ablation member (514) and a first passageway (576) within a first delivery member (510), and within a second passageway (577) within a second delivery member (512). More particularly, FIG. 5 shows ablation member (514) to include an intermediate portion (594) which is located between first and second end portions (518,520) and which includes one or more ablation electrodes (522). The first end portion (518) of ablation member (514) is slideably engaged with adjustable positioning within passageway (576) along the first delivery member (510) and through the first distal port (578) located in the distal tip (589) of first delivery member (510). The second end portion (520) is slideably engaged with adjustable positioning within passageway (577) along the second delivery member (512) and through a second distal port (579) located at the distal tip (590) of the second delivery member (512). According to this assembly, the length and positioning of ablation member (514) between the first and second delivery members (510,512) is adjustable from either side or both sides (either by adjusting the relative position of the first end portion along the first delivery member or of the second end portion along the second delivery member). In addition, passageways and actuating members may extend along each of the first and second end portions of the ablation member.

Moreover, according to the assembly shown in FIG. 5, one conduit fluid passageway (532) may extend from the first proximal end portion (582), which extends externally beyond the first delivery member (510), through ablation member (514), to the second proximal end portion (583), which extends externally beyond the second delivery member (512). In this aspect, the passageway (532) is thermally coupled to the ablation electrode(s) (522) and is adapted to cool the ablation electrode(s) (522) when heated during ablation and when fluid is allowed to flow through the fluid passageway, as is shown by way of example, by arrows pointing into the passageway at the first proximal end portion (582) and out of passageway at the second proximal end portion (583).

Still further to the variation shown in FIG. 5, distal ports (578,579) are shown at the distal tips (589,590) of first and second delivery members (510,512), wherein the distal tips (589,590) are further shown to include radiopaque markers, such as by use of radiopaque metal bands or by metal powder loaded polymeric material.

Figure 6:
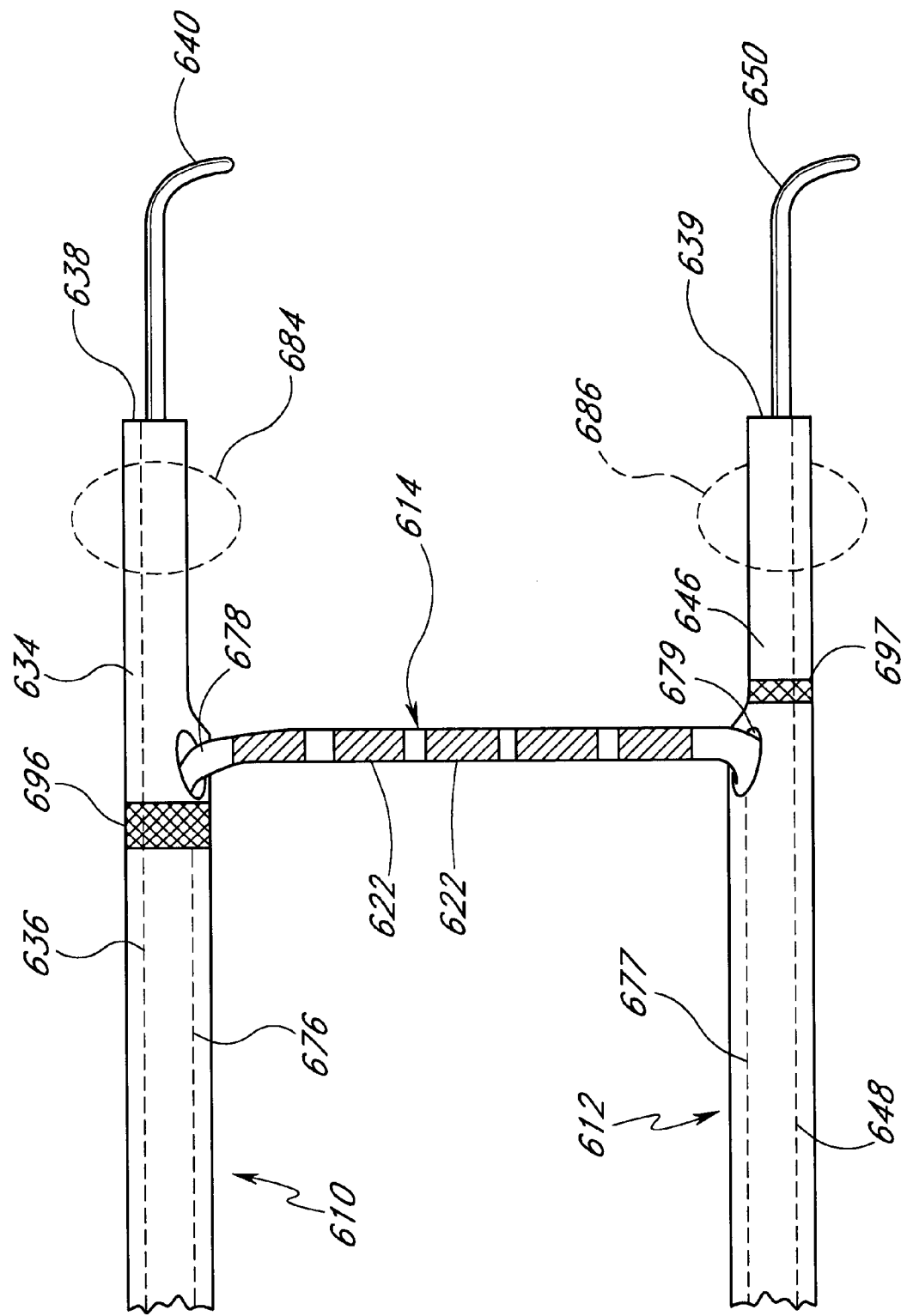
FIG. 6 shows a perspective view of another embodiment of the tissue ablation assembly of the present invention.

The assembly shown in FIG. 6 includes first and second delivery members (610,612) with guidewire tracking members (634,646) engaged over guidewires (640,650), and further provides dual-coaxial engagement within those delivery members (610,612) with ablation member (614), as shown previously in FIG. 5. However, according to the variation shown in FIG. 6, the distal ports (678,679) to the respective passageways (676,677) through which first and second end portions (618,620) of ablation member (614) are respectively engaged are positioned proximally of first and second distal guidewire ports (638,639), as is identified during use by way of radiopaque markers (696,697) that are further shown on proximal and distal sides of ports (678, 679), respectively. Further shown in shadow in FIG. 6, the first and second anchors (684,686) provided in part by the two elongate guidewire tracking members (634,646) of the delivery members (610,612) may further include expandable members, which are believed to be particularly well suited to this design by virtue of the extensions of the guidewire tracking members distally beyond the ablation member.

In an alternative variation not shown, it is further contemplated that the portion of the elongate body which forms the guidewire tracking member for either delivery member may also terminate at a distal port that is located proximally of the distal port of the passageway through which the ablation member is slideably engaged.

The tissue ablation assembly shown in FIG. 7A is illustrative of a variation which is believed to be readily combinable with the other variations of the embodiments. FIG. 7A shows a similar assembly to that just shown and described previously by reference to FIG. 5, except that the distal end portions of the respective delivery catheters have curved shapes. These shaped regions (711,713) are adapted to point the first and second delivery members (710,712) toward the posterior wall of an atrium when introduced through a transeptal delivery sheath seated across the fossa ovalis (not shown). The first and second delivery members (710, 712) are shown in shadow within delivery sheath (792).

FIGS. 7B–C schematically show alternative shaft configurations for first and second delivery members (710,712) shown in FIG. 7A, and include, respectively, two round delivery members (710,712) within an ovular delivery sheath (792), or two ovular delivery members (710,712) in a round delivery sheath (792). Conventional round shaft designs within round delivery sheath lumens are also considered acceptable, and in any case, all of these alternative variations apply equally as suitable substitutes for the other embodiments shown to include two delivery members with elongate tubular members in side-by-side arrangement within a delivery sheath.

FIGS. 7D–G show various modes for a further delivery sheath/tissue ablation device assembly embodiment, wherein the delivery sheath or catheter (792) includes a wall (795) that separate first and second delivery passageways (797, 798). According to these modes, first and second delivery passageways (797, 798) are adapted to house first and second guidewires (740, 750) and respectively engaged first and second delivery members (710, 712). Wall (795) is constructed to allow relative separation and isolation between these members in their respectively engaged passageways in order to prevent entanglement during delivery. However, the wall (795) is further constructed to be deflectable in order to allow the ablation member (714) extending between delivery members (710, 712) to bridge between the passageways (797, 798) during delivery of the ablation member (714) through the delivery catheter (792) and into the atrium for ablation.

More specifically, the wall (795) may be constructed in many alternative modes in order to achieve the feature just described, which is to provide relative isolation of the delivery passageways when only the respective guidewires or elongate bodies of the delivery members are housed within those passageways, but also to allow such isolation to be selectively broken such that the ablation member can bridge between these same passageways during delivery into the atrium.

Figure 7D:
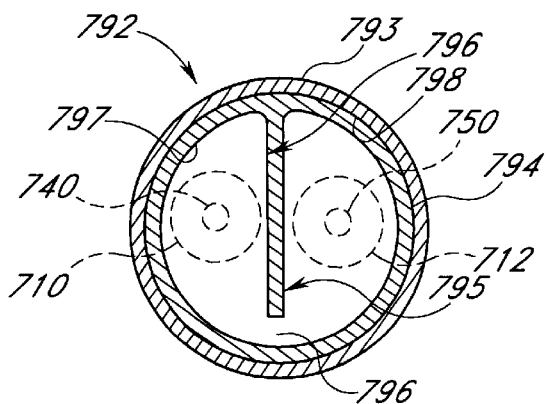
FIG. 7D shows a cross sectional view of a left atrial delivery catheter having first and second passageways which are separated by a deflectable wall, and shows in shadowed view first and second guidewires respectively engaged within first and second delivery members of a tissue ablation device, which first and second delivery members are respectively engaged within the first and second passageways and are separated by the wall.

For example, FIG. 7D shows wall (795) to be broken at a separation (796). According to this construction, where only the guidewires (740, 750) or delivery members (710, 172) are housed within passageways (797, 798), wall (795) is constructed to retain its shape to substantially transect the lumen formed by delivery catheter (792) and maintain the relative isolation and integrity between the two passageways (797, 798). However, where the ablation member (714) is also housed within delivery catheter (792), the wall (795) is pushed aside within the delivery catheter lumen, as shown in slightly varied modes in FIGS. 7E–F. It is contemplated by reference to the FIGS. 7D–G as a whole that the passageways (797, 798) may be common when the wall (795) is deflected according to the embodiments shown.

Figure 7E:
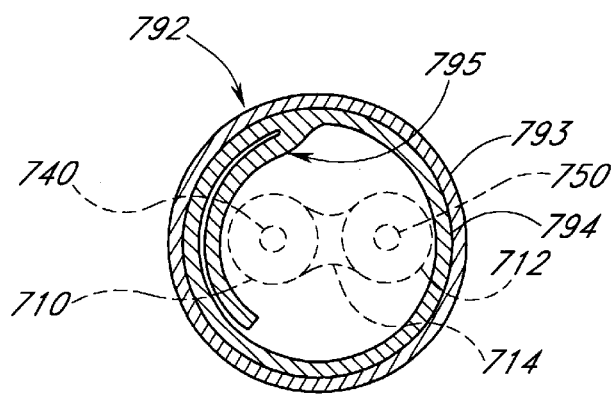
FIG. 7E shows a similar cross-sectional view of a left atrial delivery catheter and tissue ablation device assembly as shown in FIG. 7D, although showing one mode of operation wherein the wall is deflected to one side of the delivery catheter and an ablation member is shown in shadowed view to extend between the first and second delivery members, thereby bridging between the first and second passageways.
Figure 7F:
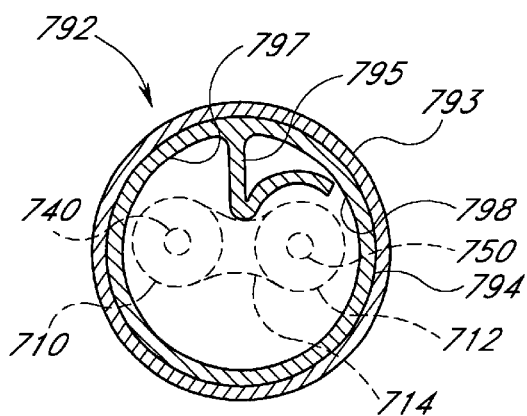
FIG. 7F shows a similar cross-sectional view as shown in FIG. 7E, and shows a different mode for the wall as it deflects within the delivery catheter to allow the ablation member to bridge between the first and second passageways.
Figure 7G:
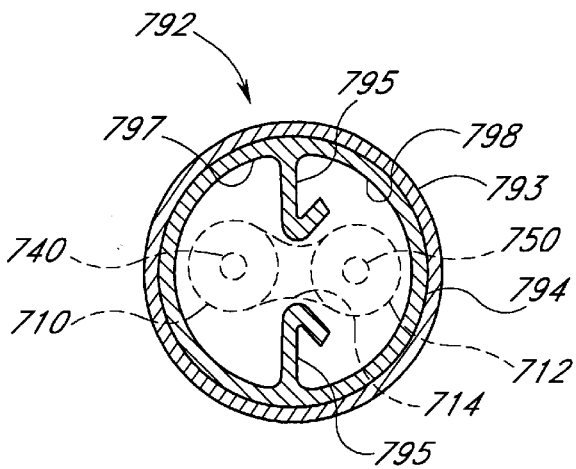
FIG. 7G shows a similar cross-sectional view as shown in FIGS. 7E–F, and shows still a further mode of construction and operation for the wall as it deflects to allow the ablation member to bridge between the first and second passageways.

Other modes of construction for wall (795) may also be suitable substitutes for that shown and described by reference to FIGS. 7D–E. In one further illustrative example, wall (795) may be secured at each of its ends to the tubular wall of delivery catheter (792), with a break or separation along an intermediate region of the wall within the delivery catheter lumen. A further more detailed example of this variation is shown at separation (796) in FIG. 7D. This embodiment is shown in a further mode of use in FIG. 7G, wherein ablation member (714) is shown to bridge between passageways (797, 798) between two separate wall portions (795, 795) that are deflected.

It is also further contemplated that such deflectability may be achieved with a wall construction that does not have literal "separations" to allow for the bridging of the ablation member between the passageways. For example, a frangible wall construction may be suitable, wherein the wall has structural integrity but has a weak point that is adapted to break or shear when the ablation member is forced along and within the inner lumen of the delivery catheter.

FIGS. 7D–G also illustrate one particular construction for delivery catheter (792), wherein an outer tubing (793) is disposed over an inner tubing (794). According to this construction, outer tubing (793) may have a first construction and material composition which provides the structural integrity necessary for the delivery catheter (792) to be delivered into the atrium during use. Inner tubing (794) may be therefore chosen merely as a "liner" in order to provide the wall structure as described, and may be one extrusion or tubing (as shown in the Figures), or may be two separate tubings that are adjoined in a manner resulting in the desired passageway and wall construction for the overall assembly. In any event, the separation or frangibility of the wall may be inherent in the construction of the inner tubing (794), such as by designing a separation into the tubing extrusion or formation itself, or may be post-processed, such as by cutting or scoring the desired separation or frangible portion after formation of the tubing. In one particular embodiment for inner tubing (794), a thin-walled polymer is used, where may or may not be the same polymer used for outer tubing (793), and in the latter case may be for example a thin-walled fluoropolymer lining, such as a PTFE lining. Still further, one uniform wall construction may also be a suitable substitute for the outer/inner tubing variation just described by reference to the particular, exemplary embodiment in the Figures.

The modes for the delivery catheter (792) variously shown throughout FIGS. 7A–G are believed to be highly desirable for use in combination with the "dual-delivery member" tissue ablation device assemblies herein shown and described. It should be apparent to those skilled in the art, however, that the above-described delivery catheter or sheath construction with a frangible or separated wall can readily be applied in other applications and designed to accommodate other types of delivery members.

The tissue ablation assemblies shown in FIG. 8 exemplify further variations, wherein similar assemblies to that previously shown and described by reference to FIG. 3 are provided in modified form. According to the variation shown in FIG. 8A, the integration of the ablation member and the second delivery member described in FIG. 3, is replaced by a separate guidewire tracking member (846), which serves as the second delivery member (812), wherein the guidewire tracking member is adapted to slideably engage and track over a guidewire (850) as an anchor for the second end portion (820) of ablation member (814). This assembly is further modified in FIG. 8B wherein the guidewire tracking member (834) of the first delivery member (810) extends along only a distal portion of this delivery member (810), such that guidewire (840) is only engaged along a portion of the delivery member's length. Also encompassed within this embodiment, but not shown in FIG. 8B, is that the guidewire tracking member (846) of the second delivery member (812) extends along only a distal portion of delivery member (812), such that guidewire (850) is only engaged along a portion of this delivery member's length.

Figure 8A:
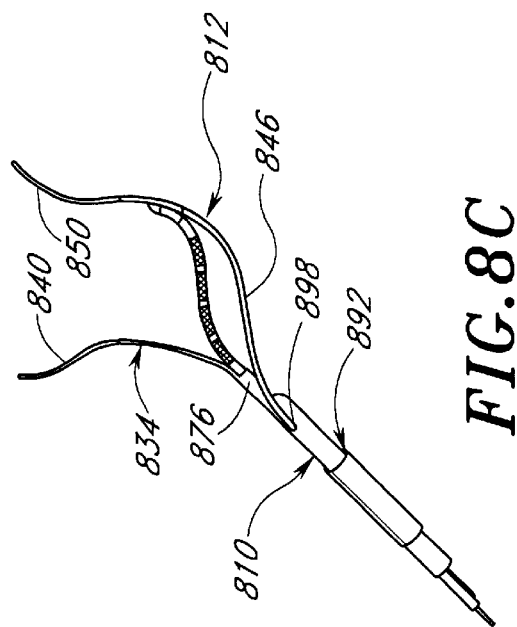
FIG. 8A is a perspective view of another tissue ablation assembly of the present invention illustrating delivery through a transeptal delivery sheath.
Figure 8C:
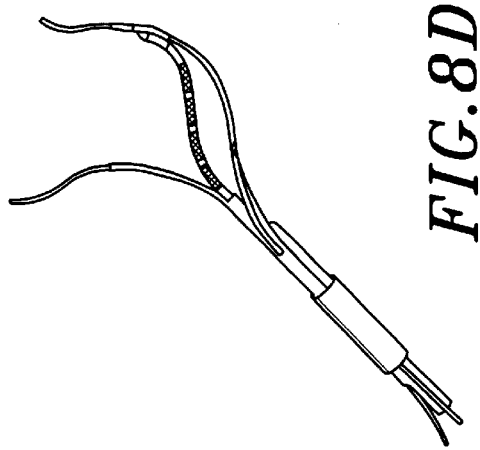
FIG. 8C shows a perspective view of another variation of the tissue ablation assembly shown in FIG. 8A.
Figure 8B:
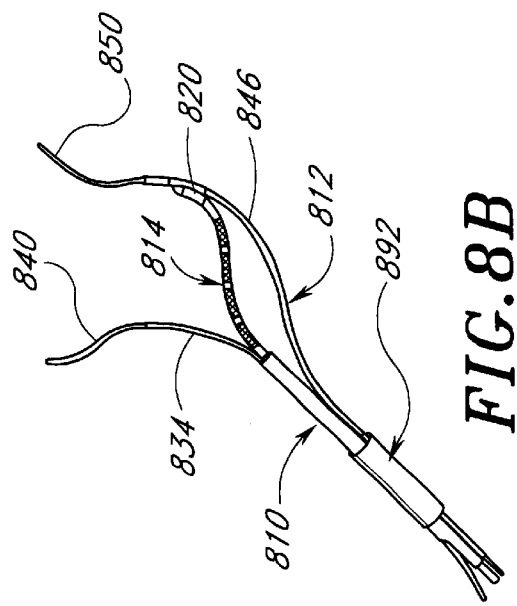
FIG. 8B is a perspective view illustrating a variation of the tissue ablation assembly shown in FIG. 8A.
Figure 8D:
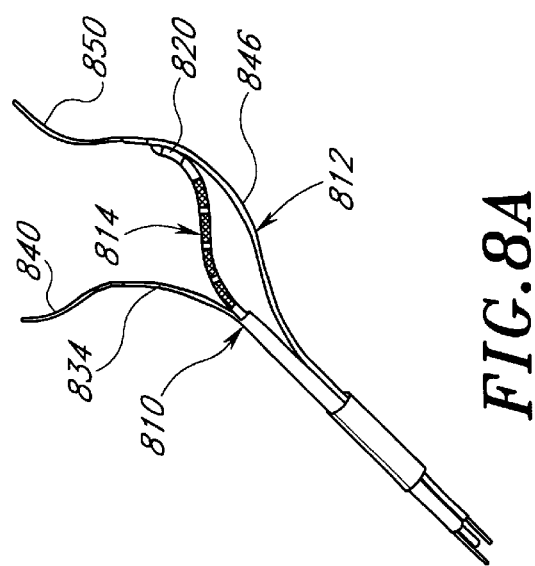
FIG. 8D is a perspective view of another variation of the assembly shown in FIG. 8C.

The tissue ablation assembly shown in FIGS. 8C and 8D further modify the previous embodiments, to include the coaxial engagement of the guidewire tracking members for both first and second delivery members and the ablation member. In this embodiment, the first end portion (818) of the ablation member is coaxially engaged within a first passageway (876) in delivery member (810). The guidewire tracking member (834) along first delivery member (810) includes a second passageway engaged over a wire (840). The first delivery member (810) includes still a third passageway (898) with a second delivery member coaxially engaged. The second delivery member also includes a second guidewire tracking member (846) over a second wire (850). In FIG. 8C, the guidewires are engaged along substantially the entire length of the guidewire tracking members. In contrast, in FIG. 8D, the guidewires are only engaged along a distal portion of the guidewire tracking members.

Figure 9:
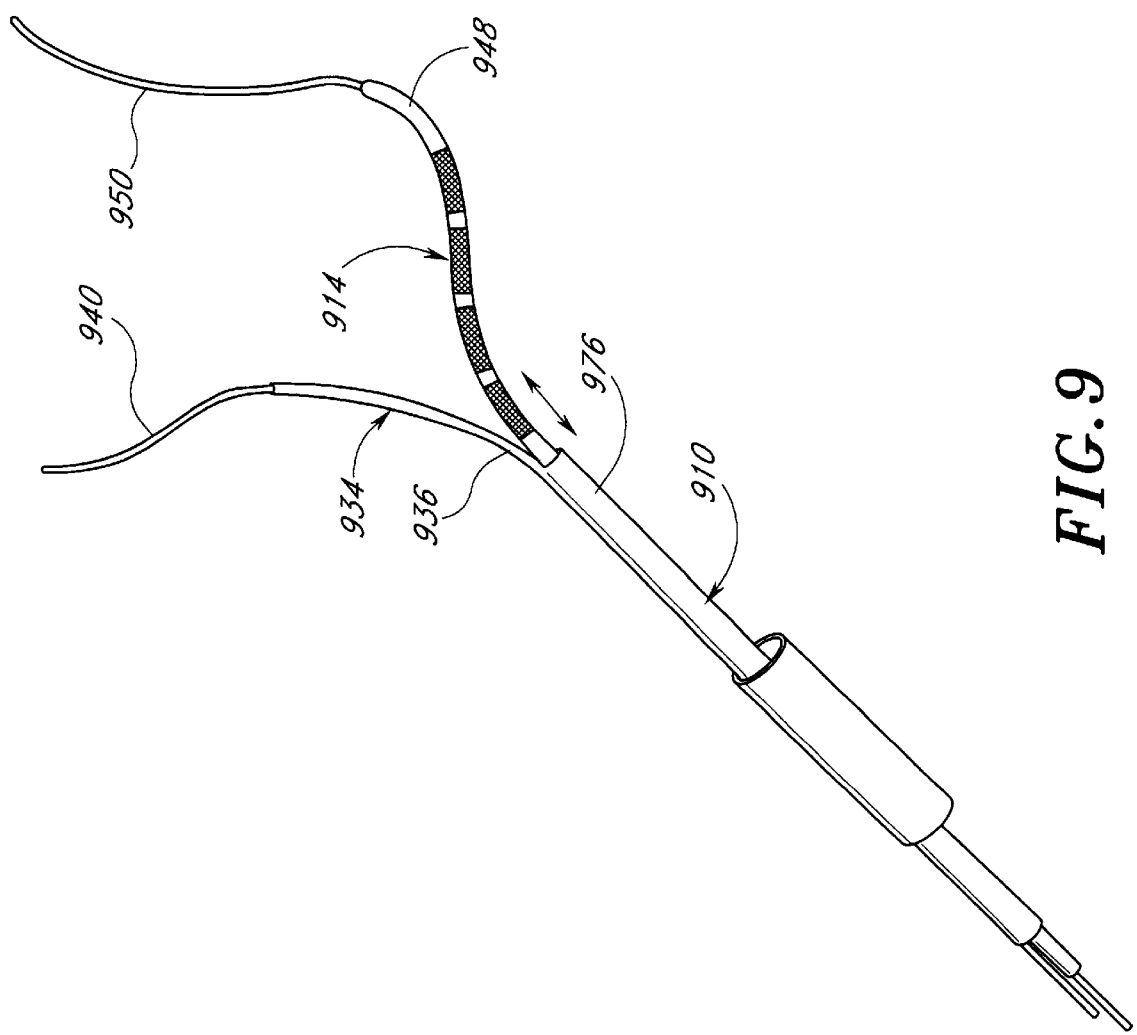
FIG. 9 shows a perspective view of another tissue ablation assembly of the invention during delivery through a transeptal delivery sheath.

The tissue ablation assembly of FIG. 9 includes a first delivery member (910) with two passageways (936,976). Passageway (936) ends in a distal guidewire port (938) and forms guidewire tracking member (934) over a guidewire (940) as a first anchor. Passageway (976) terminates distally in a distal port (978) located proximally of distal guidewire port (938). Ablation member (914) is slideably engaged within passageway (976) as similarly described for previous ablation members in FIGS. 3 and 8, except that the ablation member (914) in FIG. 9 further includes a passageway (948) running its length which tracks over a second guidewire (950) thereby providing a second anchor.

In the tissue ablation assembly shown in FIG. 10A, effectively one continuous member forms first and second delivery members with anchors and an ablation member strung therebetween. An elongate body (1009) has a first end portion (1082) and a second end portion (1083), both extending along a delivery sheath lumen (1092) in a side-by-side arrangement. A first passageway (1076) extends along the first end portion (1082) and terminates adjacent to an ablation member (1014) in a first distal port (1038), which is pictured within the right superior pulmonary vein ostium (101). The second end portion has a second passageway (1077) terminating distally adjacent to the ablation member (1014) in a second distal port (1039), which is pictured in the adjacent left superior pulmonary vein ostium (102). The simplicity of this design allows for two guidewire tracking members over first and second guidewires (1040, 1050) and provides anchors for both ends of ablation member (1014) along the length of tissue to be ablated.

It is further contemplated (shown in shadow), that another guidewire (1045) may exit another port (1081) in the elongate member (1009), at or adjacent to the left inferior pulmonary vein ostium (103), wherein an additional vertical ablation element (1015) is provided, such that the ablation element (1015) spans the linear distance between the superior and inferior left pulmonary vein ostia. Thus, one of skill in the art will readily recognize that further modification of the ablation assembly shown in FIG. 9A, to include an additional guidewire and additional ablation elements, may facilitate the induction of a four-sided closed ablation lesion connecting the four pulmonary vein ostia; the right inferior pulmonary vein ostium (104) is also pictured. Referring to FIG. 10B, the ablation assembly is modified such that the guidewires are only engaged along a distal portion of the elongate body (1009).

FIGS. 10C–D, depict another tissue ablation assembly during delivery through a transeptal delivery sheath (1092), and shows an ablation member (1014) which includes a proximal portion (1083) that forms a guidewire tracking member (1046) extending proximally in a side-by-side arrangement in parallel with a guidewire tracking member (1034) of a delivery member (1010) along the delivery sheath. FIGS. 10C and D further show each of the guidewire tracking members (1034,1046) to include a distal port into a passageway through which a guidewire is slideably engaged substantially along the end portion's length, and further shows the intermediate portion (1094) to include shaped regions (1011,1013) located at or adjacent to each of the distal ports (1038,1039) such that each shaped region is adapted to engage a vessel extending from an atrial wall while the ablation element is engaged along a length of atrial wall tissue extending between the vessels' ostia. FIG. 10D is similar to the assembly shown in FIG. 10C, except showing the first and second guidewire tracking members (1034,1046) to extend along only a distal region of the respective end portion.

FIG. 11A shows a perspective view of another tissue ablation assembly that includes an ablation member (1114) with a proximal end portion (1118) that is slideably engaged within a passageway (1176) extending along a first delivery member (1110) that further includes a guidewire tracking member (1134) slideably engaged over a guidewire (1140), and also shows a predetermined length of the distal end portion of the ablation member, which includes an ablation element, extending a predetermined distance distally from the passageway through a distal port (1178). The predetermined length of the distal end portion of the ablation member has a predetermined shape which is adapted, as shown in FIG. 11B, to be secured to a length of atrial wall tissue from a predetermined location when the ablation member (1114) is anchored by the guidewire (1140) at or adjacent to the predetermined location. The anchoring may optionally be enhanced by operation of an expandable member (1184) on the guidewire tracking member (1134).

Figure 12:
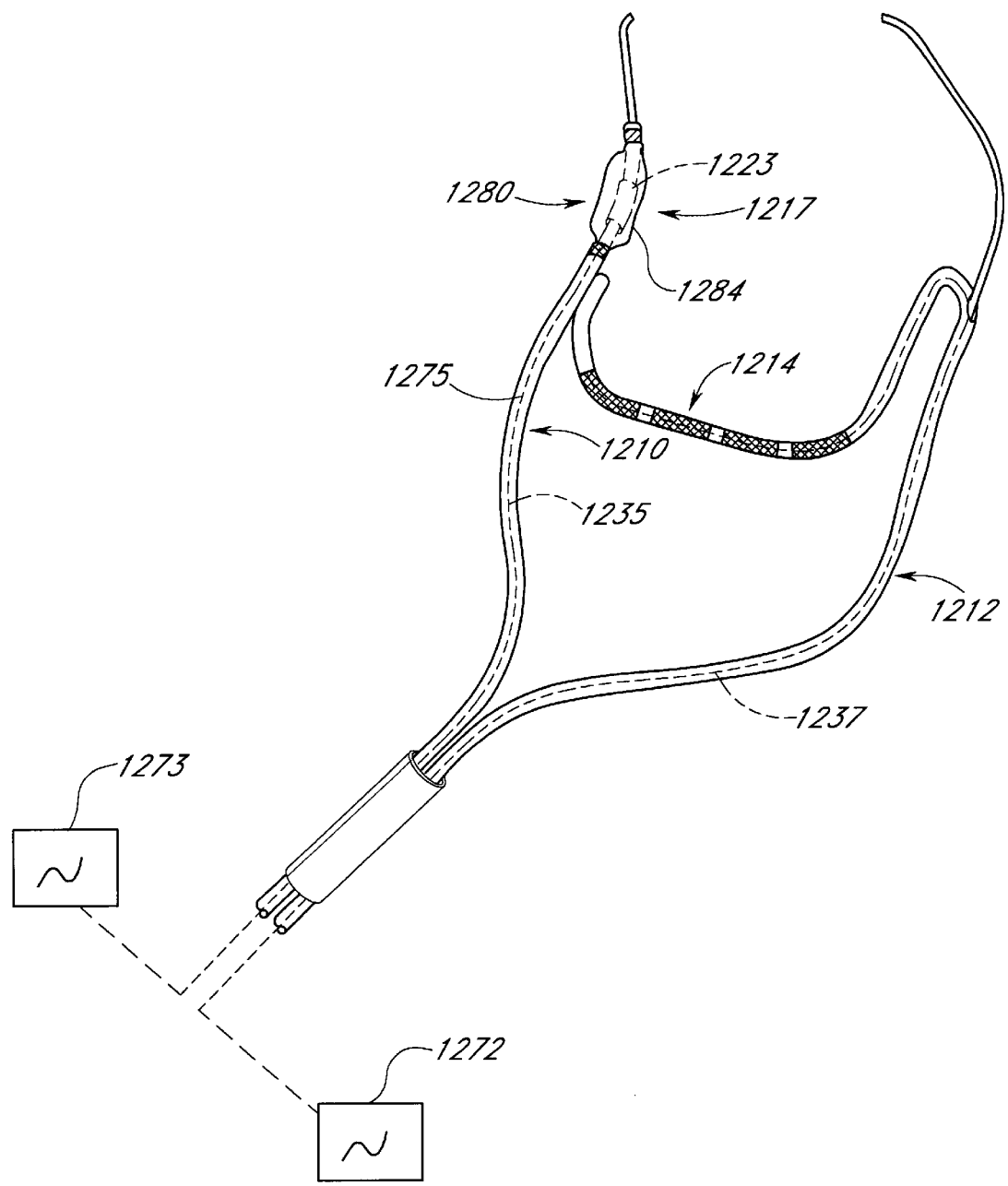
FIG. 12 shows a perspective view of a tissue ablation assembly similar to that shown in FIG. 10C, except further including a circumferential ablation member in combination with a linear ablation member in an overall catheter assembly.

FIGS. 12 and 13A–E show various specific embodiments of an ablation assembly which utilizes both a linear ablation member (1214) and a circumferential ablation element (1217). These ablation elements (1214,1217) may comprise any of the ablation devices discussed above. In an exemplary mode, as illustrated in FIG. 12, the ablation member (1214) has a linear configuration and the circumferential ablation element (1217) utilizes an acoustic energy source that radially emits a collimated energy beam in a circumferential pattern. The present linear and circumferential ablation elements (1214,1217) have particular utility in connection with forming linear and circumferential lesions along a posterior wall of the left atrium and within or about one of the associated pulmonary vein ostia (or within the vein itself) in order to form conductive blocks. This application of the present ablation assembly, however, is merely exemplary, and it is understood that those skilled in the art can readily adapt the present ablation device assembly for applications in other body spaces.

The ablation assembly is principally configured in accordance with the disclosure set forth above in connection with FIG. 10C, with the exception of the addition of the circumferential ablation element (1217). Accordingly, the foregoing description should be understood as applying equally to the present mode, except where noted otherwise.

In the illustrated embodiment, the circumferential ablation element (1217) includes a source of acoustic energy, an ultrasound transducer (1223), and an anchoring device (1284) that anchors the transducer (1223) within the targeted body space (e.g., pulmonary vein ostium). The anchoring device (1284) may also couple the transducer (1223) to the targeted tissue site. Both the anchor (1284) and the transducer (1223) are positioned at a distal end portion (1280) of one of the delivery members (1210,1212) of the ablation device assembly.

In one mode, the anchoring device (1284) comprises an expandable member that also positions (i.e., orients) the transducer (1223) within the body space; however, other anchoring and positioning devices may also be used, such as, for example, a basket mechanism. In a more specific form, the transducer (1223) is located within the expandable member (1284) and the expandable member (1284) is adapted to engage a circumferential path of tissue either about or along a pulmonary vein in the region of its ostium or along a left atrial posterior wall. The transducer (1223) in turn is acoustically coupled to the wall of the expandable member (1284), and thus to the circumferential region of tissue engaged by the expandable member wall, when actuated by an acoustic energy driver (1273) to emit a circumferential and longitudinally collimated ultrasound signal. The linear ablation member (1214) is operated by an actuator (1272).

The use of acoustic energy, and particularly ultrasonic energy, offers the advantage of simultaneously applying a dose of energy sufficient to ablate a relatively large surface area within or near the heart to a desired heating depth without exposing the heart to a large amount of current. For example, a collimated ultrasonic transducer can form a lesion, which has about a 1.5 mm width, about a 2.5 mm diameter lumen, such as a pulmonary vein, and of a sufficient depth to form an effective conductive block. It is believed that an effective conductive block can be formed by producing a lesion within the tissue that is transmural or substantially transmural. Depending upon the patient, as well as the location within the pulmonary vein ostium, the lesion may have a depth of 1 millimeter to 10 millimeters. It has been observed that the collimated ultrasonic transducer can be powered to provide a lesion having these parameters so as to form an effective conductive block between the pulmonary vein and the posterior wall of the left atrium.

With specific reference now to the embodiment illustrated in FIGS. 13A through 13D, the distal end portion (1380) of one of the delivery members (1310) includes an elongate body (1309) with proximal and distal sections (1353,1355), an expandable balloon (1384) located along the distal end portion (1380), and a circumferential ultrasound transducer (1323) which forms a circumferential ablation member that is acoustically coupled to the expandable balloon (1384). In more detail, FIGS. 13A–C variously show the elongate body section (1309) to include a guidewire lumen (1336), an inflation lumen (1385), and an electrical lead lumen (1375). The ablation device, however, can be of a self steering type rather than an over-the-wire type device, as noted below.

Each lumen extends between a proximal port (not shown) and a respective distal port, which distal ports are shown as a distal guidewire port (1338) for the guidewire lumen (1336), a distal inflation port (1387) for the inflation lumen (1385), and the distal lead port (1388) for electrical lead lumen (1375). Although the guidewire, inflation and electrical lead lumens are generally arranged in a side-by-side relationship, the elongate body section (1309) of the distal end portion (1380) can be constructed with one or more of these lumens arranged in a coaxial relationship, or in any of a wide variety of configurations that will be readily apparent to one of ordinary skill in the art.

In addition, the elongate body (1309) is also shown in FIGS. 13A and 13C to include an inner member (1308) that extends distally beyond the distal inflation and lead ports (1387,1388), through an interior chamber formed by the expandable balloon (1384), and distally beyond the expandable balloon (1384) where the elongate body (1309) terminates in a distal tip. The inner member (1308) forms the distal region for the guidewire lumen (1336) beyond the inflation and lead ports, and also provides a support member for the cylindrical ultrasound transducer (1323) and for the distal neck of the expansion balloon (1384), as described in more detail below.

One more detailed construction for the components of the elongate body section (1309) which is believed to be suitable for use in transeptal left atrial ablation procedures is as follows. The elongate body (1309) itself may have an outer diameter provided within the range of from about 5 French to about 10 French, and more preferably from about 7 French to about 9 French. The guidewire lumen preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen preferably has an inner diameter of 0.040 inch to about 0.042 inch. In addition, the inflation lumen preferably has an inner diameter of about 0.020 inch in order to allow for rapid deflation times, although may vary based upon the viscosity of inflation medium used, length of the lumen, and other dynamic factors relating to fluid flow and pressure.

In addition to providing the requisite lumens and support members for the ultrasound transducer assembly, the elongate body section (1309) of the delivery member must also be adapted to be introduced into the left atrium such that the distal end portion with the balloon (1384) and transducer (1323) may be placed within the pulmonary vein ostium in a percutaneous translumenal procedure, and even more preferably in a transeptal procedure as otherwise herein provided. Therefore, the distal end portion (1380) is preferably flexible and adapted to track over and along a guidewire seated within the targeted pulmonary vein. In one further more detailed construction which is believed to be suitable, the proximal end portion is adapted to be at least 30% more stiff than the distal end portion. According to this relationship, the proximal end portion may be suitably adapted to provide push transmission (and possibly torque transmission) to the distal end portion while the distal end portion is suitably adapted to track through bending anatomy during in vivo delivery of the distal end portion of the device into the desired ablation region.

At least a distal portion of the delivery member (1310) tracks over a guide wire (1340). Notwithstanding the specific device constructions just described, other variations of the delivery member are also contemplated. For example, while the illustrated mode is shown as an "over-the-wire" catheter construction, other guidewire tracking designs may be suitable substitutes, such as, for example, catheter devices which are known as "rapid exchange" or "monorail" variations wherein the guidewire is only housed coaxially within a lumen of the catheter in the distal regions of the catheter.

In another example, a deflectable tip design may also be a suitable substitute and which is adapted to independently select a desired pulmonary vein and direct the transducer assembly into the desired location for ablation. Further to this latter variation, the guidewire lumen and guidewire shown in FIG. 13A may be replaced with a "pullwire" lumen and associated fixed pullwire which is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

More specifically regarding the expandable balloon (1384) as shown in varied detail between FIGS. 13A and 13C, a central region (1391) is generally coaxially disposed over the inner member (1308) and is bordered at its end neck regions by proximal and distal adaptations (1393,1395). The proximal adaptation (1393) is sealed over elongate body section (1309) proximally of the distal inflation and the electrical lead ports (1387,1388), and the distal adaptation (1395) is sealed over inner member (1309). According to this arrangement, a fluid tight interior chamber is formed within expandable balloon (1384). This interior chamber is fluidly coupled to a pressurizeable fluid source (not shown) via the inflation lumen (1387). In addition to the inflation lumen (1385), the electrical lead lumen (1375) also communicates with the interior chamber of expandable balloon (1384) so that the ultrasound transducer (1323), which is positioned within that the chamber and over the inner member (1308), may be electrically coupled to an ultrasound drive source or actuator, as will be provided in more detail below.

The expandable balloon (1384) may be constructed from a variety of known materials, although the balloon (1384) preferably is adapted to conform to the contour of a pulmonary vein ostium. For this purpose, the balloon material can be of the highly compliant variety, such that the material elongates upon application of pressure and takes on the shape of the body lumen or space when fully inflated. Suitable balloon materials include elastomers, such as, for example, but without limitation, silicone, latex, or low durometer polyurethane (for example a durometer of about 80A).

In addition or in the alternative to constructing the balloon of highly compliant material, the balloon (1384) can be formed to have a predefined fully inflated shape (i.e., be preshaped) to generally match the anatomic shape of the body lumen or space in which the balloon is inflated. For instance, as described below in greater detail, the balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Notwithstanding the alternatives which may be acceptable as just described, the balloon (1384) is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taught configuration. In other words, "expansion" is herein intended to relate to change in diameter that is attributable to the material compliance in a stress strain relationship. In one more detailed construction which is believed to be suitable for use in most conduction block procedures in the region of the pulmonary veins, the balloon is adapted to expand under a normal range of pressure such that its outer diameter may be adjusted from a radially collapsed position of about 5 millimeters to a radially expanded position of about 2.5 centimeters (or approximately 500% expansion ratio).

The ablation member (1323), which is illustrated in FIGS. 13A–D, takes the form of an annular ultrasonic transducer applicator. In the illustrated embodiment, the annular ultrasonic transducer applicator (1323) has a unitary cylindrical shape with a hollow interior (i.e., is tubular shaped); however, the transducer applicator can have a generally annular shape and be formed of a plurality of segments. For instance, the transducer applicator can be formed by a plurality of tube sectors that together form an annular shape. The generally annular shape can also be formed by a plurality of planar transducer segments which are arranged in a polygon shape (e.g., hexagon). In addition, although in the illustrated embodiment the ultrasonic transducer comprises a single transducer element, the transducer applicator can be formed of a multi-element array, as described in greater detail below.

Figure 13E:
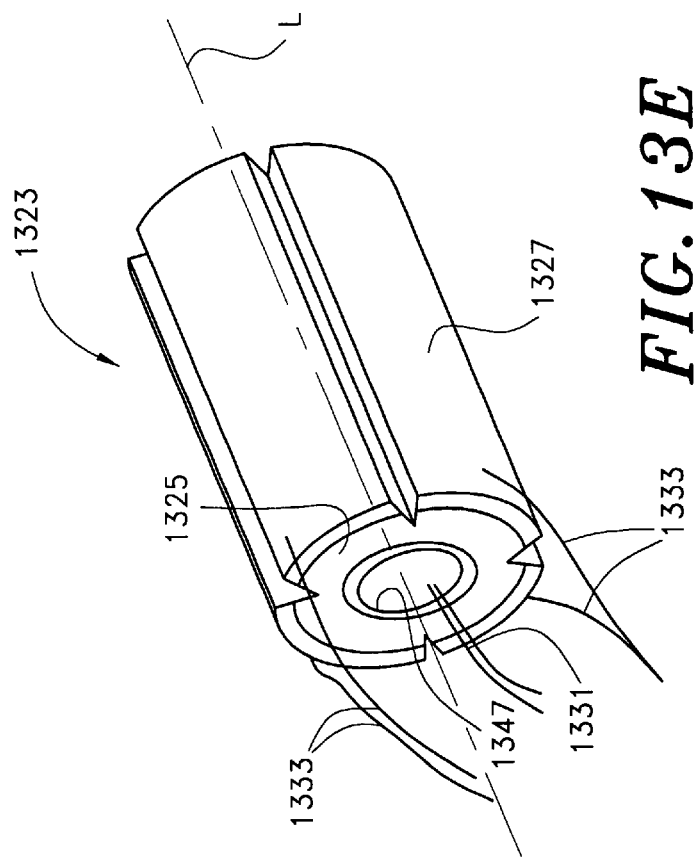
FIG. 13E shows an angular perspective view of another cylindrical ultrasound transducer which is adapted for use in the circumferential ablation element shown in FIGS. 13A and 13C.
Figure 13D:
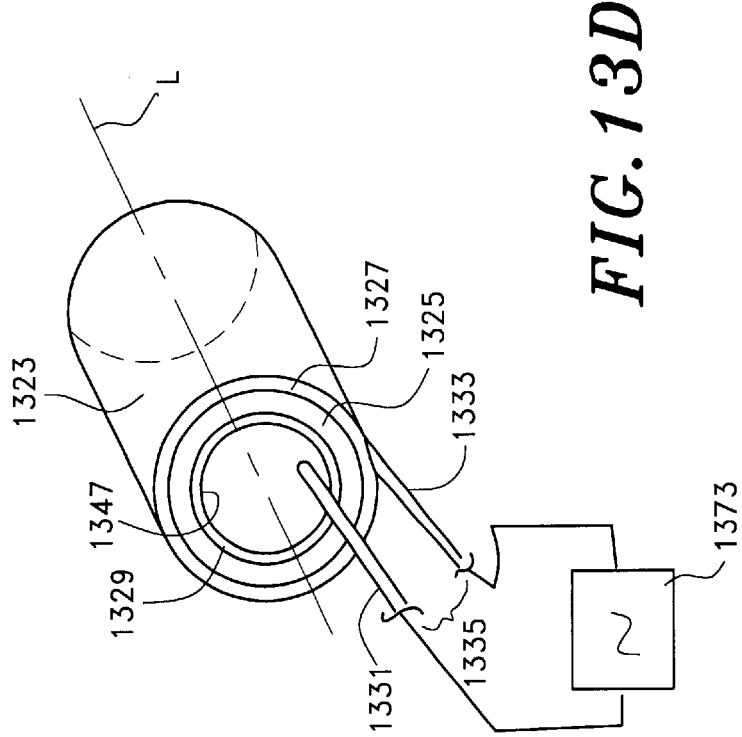
FIG. 13D shows an angular perspective view of a cylindrical ultrasound transducer which is adapted for use in the circumferential ablation element shown in FIGS. 13A and 13C.

As is shown in detail in FIG. 13D, the cylindrical ultrasound transducer (1323) includes a tubular wall which includes three concentric tubular layers. A central layer (1325) has a tubular shaped member of a piezoceramic or piezoelectric crystalline material. This transducer element preferably is made of type PZT-4, PZT-5 or PZT-8, quartz or Lithium-Niobate type piezoceramic material to ensure high power output capabilities. These types of transducer materials are commercially available from Stavely Sensors, Inc. of East Hartford, Connecticut, or from Valpey-Fischer Corp. of Hopkinton, Massachusetts.

The outer and inner tubular members (1327,1329) enclose the central layer (1325) within their coaxial space and are constructed of an electrically conductive material. In the illustrated embodiment, these outer and inner members which form the transducer electrodes (1327,1329) comprise a metallic coating, and more preferably a coating of nickel, copper, silver, gold, platinum, or alloys of these metals.

One more detailed construction for a cylindrical ultrasound transducer (1323) for use in the present application is as follows. The length D of the transducer applicator (1323) or transducer applicator assembly (e.g., multi-element array of transducer elements) desirably is selected for a given clinical application, but is less than a length D of the balloon (1384) that contacts the tissue. In connection with forming circumferential conduction blocks in cardiac or pulmonary vein wall tissue, the transducer length can fall within the range of approximately 2 mm up to greater than 10 mm, and preferably equals about 5 mm to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transeptally), for proper placement and location within a particular body space, and for achieving a desired ablation effect. In the given application within or proximate of the pulmonary vein ostium, the transducer preferably has an outer diameter within the range of about 1.8 mm to greater than 2.5 mm. It has been observed that a transducer with an outer diameter of about 2 mm generates acoustic power levels approaching 20 Watts per centimeter radiator or greater within myocardial or vascular tissue, which is believed to be sufficient for ablation of tissue engaged by the outer balloon for up to about a 2 cm outer diameter of the balloon. For applications in other body spaces, the transducer applicator may have an outer diameter within the range of about 1 mm to greater than 3–4 mm (e.g., as large as 1 to 2 cm for applications in some body spaces).

The central layer (1325) of the transducer applicator (1323) has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer in the illustrated application preferably operates within the range of about 5 MHz to about 20 MHz, and more preferably within the range of about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

The transducer applicator (1323) is vibrated across the wall thickness to radiate collimated acoustic energy in a radial direction. For this purpose, as best seen in FIGS. 13A and 13D, the distal ends of electrical leads (1331,1333) are electrically coupled to outer and inner tubular members or electrodes (1327,1329), respectively, of the transducer (1323), such as, for example, by soldering the leads to the metallic coatings or by resistance welding. In the illustrated embodiment, the electrical leads are 4–8 mil (0.004 to 0.008 inch diameter) silver wire or the like.

Importantly, as best understood from FIG. 12, the wire leads or lead set, indicated generally by reference numeral (1235), for the circumferential ablation element (1223) are routed through the lead lumen (1275) of the first delivery member (1210), while the wire leads or lead set (1237) for the linear ablation element (1214) are routed through one or more wire lead lumens that extends through the linear ablation member (1214) and through the second delivery member (1212). The separation of these lead sets (1235, 1237) reduces any cross-contamination or noise in the signal carried by one of the lead sets due to its proximity of the other lead set.

The proximal ends of the leads of the lead set (1235) for the circumferential ablation element (1223) are adapted to couple to an ultrasonic driver or actuator (1273), which is schematically illustrated in FIG. 12. FIGS. 13A–C further show leads as separate wires within electrical lead lumen, in which configuration the leads must be well insulated when in close contact. Other configurations for leads are therefore contemplated. For example, a coaxial cable may provide one cable for both leads which is well insulated as to inductance interference. Or, the leads may be communicated toward the distal end portion of the elongate body through different lumens which are separated by the catheter body.

Still with reference to FIG. 12, the leads of the lead sets (1237) for the linear ablation element (1214) are coupled to an ablation actuator (1272), which is configured in accordance with the above description. The ablation actuator (1272) desirably includes a current source for supplying an RF current, a monitoring circuit, and a control circuit. The current source is coupled to the linear ablation element (1214) via the lead set (1237), and to a ground patch (not shown). The monitor circuit desirably communicates with one or more sensors (e.g., temperature or current sensors) which monitor the operation of the linear ablation element (1214). The control circuit is connected to the monitoring circuit and to the current source in order to adjust the output level of the current driving the electrodes of the linear ablation element (1214) based upon the sensed condition (e.g., upon the relationship between the monitored temperature and a predetermined temperature set-point).

The ultrasonic actuator (1273) generates alternating current to power the transducer. The ultrasonic actuator (1273) drives the transducer at frequencies within the range of about 5 to about 20 MHz, and preferably for the illustrated application within the range of about 7 MHz to about 10 MHz. In addition, the ultrasonic driver (1273) can modulate the driving frequencies and/or vary power in order to smooth or unify the produced collimated ultrasonic beam. For instance, the function generator of the ultrasonic driver can drive the transducer at frequencies within the range of 6.8 MHz and 7.2 MHz by continuously or discretely sweeping between these frequencies.

The ultrasound transducer (1223) of the present embodiment sonically couples with the outer skin of the balloon (1284) in a manner which forms a circumferential conduction block in a pulmonary vein as follows. Initially, the ultrasound transducer (1223) is believed to emit its energy in a circumferential pattern which is highly collimated along the transducer's length relative to its longitudinal axis L (see FIG. 13D). The circumferential band therefore maintains its width and circumferential pattern over an appreciable range of diameters away from the source at the transducer. Also, the balloon (1284) is preferably inflated with fluid which is relatively ultrasonically transparent, such as, for example, degassed water. Therefore, by actuating the transducer while the balloon is inflated, the circumferential band of energy is allowed to translate through the inflation fluid and ultimately sonically couple with a circumferential band of balloon skin which circumscribes the balloon. Moreover, the circumferential band of balloon skin material may also be further engaged along a circumferential path of tissue which circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated.

With reference to FIG. 13E, the transducer (1323) also can be sectored by scoring or notching the outer transducer electrode and part of the central layer along lines parallel to the longitudinal axis L of the transducer (1323). A separate electrical lead connects to each sector in order to couple the sector to a dedicated power control that individually excites the corresponding transducer sector. By controlling the driving power and operating frequency to each individual sector, the ultrasonic driver can enhance the uniformity of the ultrasonic beam around the transducer, and vary the degree of heating (i.e., lesion control) in the angular dimension. Again the leads for each sector may be routed through different lumens of the two delivery members.

The ultrasound transducer just described is combined with the overall device assembly according to the present embodiment as follows. In assembly, the transducer desirably is "air-backed" to produce more energy and to enhance energy distribution uniformity, as known in the art. In other words, the inner member does not contact an appreciable amount of the inner surface of transducer inner tubular member.

For this purpose, the transducer seats coaxial about the inner member and is supported about the inner member in a manner providing a gap between the inner member and the transducer inner tubular member. That is, the inner tubular member forms an interior bore which loosely receives the inner member. Any of a variety of structures can be used to support the transducer about the inner member. For instance, spaces or splines can be used to coaxially position the transducer about the inner member while leaving a generally annular space between these components. In the alternative, other conventional and known approaches to support the transducer can also be used. For instance, O-rings that circumscribe the inner member and lie between the inner member and the transducer can support the transducer in a manner similar to that illustrated in U.S. Pat. No. 5,606,974 to Castellano. Another example of alternative transducer support structures is disclosed in U.S. Pat. No. 5,620,479 to Diederich. The disclosures of these references are incorporated herein by reference.

In the illustrated embodiment, a stand-off (1341) is provided in order to ensure that the transducer has a radial separation from the inner member to form a gap filled with air and/or other fluid. In one preferred mode shown in FIG. 13C, stand-off (1341) is a tubular member with a plurality of circumferentially spaced outer splines (1343) which hold the majority of the transducer inner surface away from the surface of the stand-off between the splines, thereby minimizing damping affects from the coupling of the transducer to the catheter. The stand-off (1341) is inserted within the inner hollow cavity (1347) of the transducer (1323).

The transducer desirably is electrically and mechanically isolated from the interior of the balloon. Again, any of a variety of coatings, sheaths, sealants, tubings and the like may be suitable for this purpose, such as those described in U.S. Pat. Nos. 5,620,479 and 5,606,974. In the illustrated embodiment, as best illustrated in FIG. 13C, a conventional sealant, such as, for example, General Electric Silicon II gasket glue and sealant, desirably is applied at the proximal and distal ends of the transducer around the exposed portions of the inner member, wires and standoff to seal the space between the transducer and the inner member at these locations. In addition, a conventional, flexible, acoustically compatible, and medical grade epoxy can be applied over the transducer. The epoxy may be, for example, Epotek 301, Epotek 310, which is available commercially from Epoxy Technology, or Tracon FDA-8.

An ultra thin-walled polyester heat shrink tubing or the like then seals the epoxy coated transducer. Alternatively, the epoxy covered transducer, inner member and standoff can be instead into a tight thin wall rubber or plastic tubing made from a material such as Teflon®, polyethylene, polyurethane, silastic or the like. The tubing desirably has a thickness of 0.0005 to 0.003 inches.

When assembling the ablation device assembly, additional epoxy is injected into the tubing after the tubing is placed over the epoxy coated transducer. As the tube shrinks, excess epoxy flows out and a thin layer of epoxy remains between the transducer and the heat shrink tubing. This layer protects the transducer surface, helps acoustically match the transducer to the load, makes the ablation device more robust, and ensures air-tight integrity of the air backing.

Although not illustrated in FIG. 13A in order to simplify the drawing, the tubing extends beyond the ends of transducer and surrounds a portion of the inner member on either side of the transducer. A filler (not shown) can also be used to support the ends of the tubing. Suitable fillers include flexible materials such as, for example, but without limitation, epoxy, Teflon® tape and the like.

Further to known ablation catheter devices and methods of the type just summarized above, early disclosures of such ablation catheter treatments include emitting direct current (DC) from an electrode on the distal end of a catheter in order to ablate the targeted tissue believed to be the focus of a particular arrhythmia. However, more recently, devices and procedures instead use radio frequency (RF) current as the energy source for tissue ablation, as disclosed in U.S. Pat. No. 5,209,229 to Gilli; U.S. Pat. No. 5,293,868 to Nardella; and U.S. Pat. No. 5,228,442 to Imran. Other energy sources which have been used in catheter-based ablation procedures are disclosed in the following references: U.S. Pat. No. 5,147,355 to Friedman et al; U.S. Pat. No. 5,156,157 to Valenta Jr, et al.; WO 93/20767 to Stem et al.; and U.S. Pat. No. 5,104,393 to Isner et al. The disclosures of these references are herein incorporated in their entirety by reference thereto.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A tissue ablation device assembly for ablating a length of tissue between first and second predetermined locations in a patient, comprising:
    a first delivery member having a distal end portion and defining a first tracking member adapted to slidably engage and track over a first guide member, the first delivery member also defining a passageway terminating in a side port proximal to a distal end;
    a second delivery member having a distal end portion; and
    an elongated ablation member having a first end portion slidably engaged in the passageway of the first delivery member and a second end portion coupled to the distal end portion of the second delivery member, the ablation member including an ablation element located at least in part between the first and second end portions of the ablation member;
    wherein the ablation member is selectively extendable from the passageway and the first and second delivery members are adapted for advancement to the first and second predetermined locations, respectively, such that the ablation element can be positioned along the length of tissue.

2. The tissue ablation device assembly of claim 1, further comprising an expandable member disposed along the distal end portion of the first delivery member distal to the side port, the expandable member being adapted for engagement in a tubular body structure.

3. The tissue ablation device assembly of claim 2, wherein the expandable member is a balloon.

4. The tissue ablation device assembly of claim 1, wherein the first guide member is a first guidewire.

5. The tissue ablation device assembly of claim 1, wherein the second end portion of the ablation member further comprises a second tracking member adapted to slidably engage and track over the second delivery member.

6. The tissue ablation device assembly of claim 5, wherein the second delivery member is a second guidewire.

7. The tissue ablation device assembly of claim 5, further comprising at least one radial enlargement located along the distal end portion of the second delivery member and sized for contacting the second end portion of the ablation member.

8. The tissue ablation device assembly of claim 1, wherein the ablation member is adapted to form a conduction block along a length of tissue between first and second pulmonary vein ostia along an atrial wall and the first delivery member is adapted for advancement into a first pulmonary vein ostium.

9. The tissue ablation device assembly of claim 8, wherein the second delivery member is adapted for advancement into a second pulmonary vein ostium.

10. The tissue ablation device assembly of claim 1, wherein the distal end portion of at least one of the delivery members further comprises a curved shape.

11. The tissue ablation device assembly of claim 1, wherein the ablation element comprises at least one electrode.

12. The tissue ablation device assembly of claim 1, further comprising a delivery sheath and wherein the first and second delivery members are adapted to be slideably engaged within the delivery sheath in a side-by-side arrangement during delivery to a treatment site.

13. The tissue ablation device assembly of claim 1, wherein the ablation element comprises an ablation length with multiple electrodes along the length.

14. The tissue ablation device assembly of claim 1, wherein the ablation element comprises at least one ultrasound transducer.

15. A tissue ablation device assembly adapted to form a linear conduction block along a length of tissue between first and second pulmonary vein ostia along an atrial wall in a patient, comprising:
    a first guidewire;
    a first delivery member having a distal end portion and defining a first tracking member adapted to slidably engage and track over the first guidewire, the first delivery member also having a passageway terminating in a side port proximal to a distal end, the distal end portion of the first delivery member being adapted for insertion into the first pulmonary vein ostium;
    a second delivery member having a distal end portion adapted for insertion into the second pulmonary vein ostium; and
    an elongated ablation member having a first end portion slidably engaged in the passageway of the first delivery member and a second end portion coupled to the distal end portion of the second delivery member, the ablation member including an ablation element located at least in part between the first and second end portions of the ablation member;
    wherein the ablation member is selectively extendable from the passageway of the first delivery member and the first and second delivery members can be manipulated to position the ablation element along the length of tissue between the first and second pulmonary vein ostia.

16. A tissue ablation device assembly adapted to form a linear conduction block along a length of tissue between first and second pulmonary vein ostia along an atrial wall in a patient, comprising:
    a first guidewire;

a delivery member having a distal end portion and a first tracking member adapted to slidably engage and track over the first guidewire, the delivery member also having a passageway terminating in a side port proximal to a distal end, the distal end portion of the first delivery member being adapted for insertion into the first pulmonary vein ostium, the delivery member having a first expandable member disposed along the distal end portion for anchoring in the first pulmonary vein ostium;

a second guidewire having a distal end portion adapted for insertion into the second pulmonary vein ostium, the second guidewire including a radial enlargement; and a single elongated ablation member having a first end portion slidably engaged in the passageway of the delivery member and a second end portion formed with a second tracking member adapted to slidably engage and track over the second guidewire, the ablation member including an ablation element located at least in part between the first and second end portions of the ablation member, the ablation member also including a second expandable member disposed along the second end portion for anchoring in the second pulmonary vein ostium;

wherein the second guidewire is independently advanceable such that the radial enlargement contacts the second end portion of the ablation member to selectively extend the ablation member from the passageway and the first and second guidewires can be manipulated to position the ablation element along the length of tissue located between the first and second pulmonary vein ostia to form a linear conduction block thereon.

* * * * *